(12) United States Patent
Power et al.

(10) Patent No.: US 7,638,480 B2
(45) Date of Patent: Dec. 29, 2009

(54) USE OF OSTEOPROTEGERIN FOR THE TREATMENT AND/OR PREVENTION OF FIBROTIC DISEASE

(75) Inventors: Christine Power, Thoiry (FR); Christine Plater-Zyberk, Geneva (CH)

(73) Assignee: Laboratoires Serono SA, Coinsins (CH)

( * ) Notice: Subject to any disclaimer, the term of this patent is extended or adjusted under 35 U.S.C. 154(b) by 715 days.

(21) Appl. No.: 10/510,876

(22) PCT Filed: Mar. 26, 2003

(86) PCT No.: PCT/EP03/50080

§ 371 (c)(1),
(2), (4) Date: Jun. 20, 2005

(87) PCT Pub. No.: WO03/084560

PCT Pub. Date: Oct. 16, 2003

(65) Prior Publication Data

US 2006/0003928 A1 Jan. 5, 2006

(30) Foreign Application Priority Data

Apr. 10, 2002 (EP) .................................. 02100364

(51) Int. Cl.
*A61K 38/18* (2006.01)
*C07K 14/51* (2006.01)
*C07K 19/00* (2006.01)
*C12N 5/00* (2006.01)
*C12N 15/00* (2006.01)

(52) U.S. Cl. ..................... 514/2; 530/399; 530/387.1; 530/387.3; 435/69.1; 435/325; 514/12

(58) Field of Classification Search .................. None
See application file for complete search history.

(56) References Cited

U.S. PATENT DOCUMENTS

| | | | |
|---|---|---|---|
| 4,588,585 A | 5/1986 | Mark et al. | |
| 4,737,462 A | 4/1988 | Mark et al. | |
| 4,879,111 A | 11/1989 | Chong | |
| 4,904,584 A | 2/1990 | Shaw | |
| 4,959,314 A | 9/1990 | Mark et al. | |
| 4,965,195 A | 10/1990 | Namen et al. | |
| 5,017,691 A | 5/1991 | Lee et al. | |
| 5,116,943 A | 5/1992 | Koths et al. | |
| 7,005,413 B1* | 2/2006 | Boyle et al. ............... | 514/2 |
| 2005/0143301 A1* | 6/2005 | Power et al. ............... | 514/12 |
| 2006/0019887 A1* | 1/2006 | Dunstan ................... | 514/12 |
| 2006/0084595 A1 | 4/2006 | Yamamoto et al. | |

FOREIGN PATENT DOCUMENTS

| | | |
|---|---|---|
| WO | WO 92/13095 | 8/1992 |
| WO | WO 98/35043 | 8/1998 |
| WO | WO 99/53942 | 10/1999 |
| WO | WO 01/17543 A3 | 3/2001 |
| WO | WO 02/46225 | 6/2002 |

OTHER PUBLICATIONS

Franklin. Current approaches to the therapy of fibrotic diseases. Biochemical Pharmacology. vol. 49, No. 3, pp. 267-273 (1995).*
Sato et al. Signal transduction by the high-affinity GM-CSF receptor: two distinct cytoplasmic regions of the common B subunit responsible for different signaling. The EMBO Journal, vol. 12, No. 11, pp. 4181-4189 (1993).*
Krane, S. M., "Is Collagenase (Matrix Metalloproteinase-1) Necessary for Bone and Other Connective Tissue Remodeling?" Clinical Orthopaedics and Related Research, vol. 313, pp. 47-53 (1995).
Takehara et al., "Localized scleroderma is an autoimmune disorder," Rheumatology, 44:274-279 (2005).
Wells, James A., "Additivity of Mutational Effects in Proteins," Biochemistry, 29(37):8509-8517 (1990).
Abraham et al., "Expression and function of surface antigens on scleroderma fibroblasts," Arthritis Rheum, 34:1164-1172 (1991).
Bucay et al., "Osteoprotegerin-deficient mice develop early onset osteoporosis and arterial calcification," Genes & Development, 12:1260-1268 (1998).
Granot et al., "Halofuginone: an inhibitor of collagen type I synthesis," Biochimica Biophys. Acta 1156:107-112 (1993).
Hattori et al., "Bleomycin induced pulmonary fibrosis in fibrinogen null mice," J. Clin. Invest. 106:1341-1350 (2000).
Heron et al., "Intracerebral Calcification in Systemic Sclerosis," Stroke, 30(10):2183-2185 (1999).
Kostenuik et al., "Osteoprotegerin: A Physiological and Pharmacological Inhibitor of Bone Resorption," Curr. Pharm Des, 7(8):613-635 (2001).
Leighton, "Drug Treatment of Scleroderma," Drugs 61(3):419-427 (2001).
Malyankar et al., "Osteoprotegerin is an $\alpha_v\beta_3$-induced, NF-κB-dependent Survival Factor for Endothelial Cells," Journal of Biological Chem., 275(28):20959-20962 (2000).
Martini et al., "Marked and Sustained Improvement Two Years After Autologous Stem Cell Transplantation in a Girl With Systemic Sclerosis," Arthritis Rheum. 42:807-811 (1999).
Mathiesen et al., "The Clinical Significance of Slightly to Moderately Increased Liver Transaminase Values in Asymptomatic Patients," Scand J Gastroenterol., 34(1):85-91 (1999).
McGaha et al., "Halofuginone, an Inhibitor of Type-1 Collagen Synthesis and Skin Sclerosis, Blocks Transforming Growth-Factor-β-Mediated Smad3 Activation in Fibroblasts," J. Invest Derm., 118:461-470 (2002).
Min et al., "Osteoprotegerin reverses osteoporosis by inhibiting endosteal osteoclasts and prevents vascular calcification by blocking a process resembling osteoclastogenesis," J. Exp. Med., 192:463-474 (2000).
Morinaga et al., "Cloning and characterization of the gene encoding human osteoprotegerin/osteoclastogenesis-inhibitory factor," Eur. J. Biochem., 254:685-691 (1998).
Salant, et al., "Heymann nephritis: Mechanisms of renal injury," Kidney Int. 35:976-984 (1989).

(Continued)

*Primary Examiner*—Christine J Saoud
*Assistant Examiner*—Regina M DeBerry
(74) *Attorney, Agent, or Firm*—Ropes & Gray LLP

(57) ABSTRACT

The invention relates to the use of osteoprotegerin for treatment and/or prevention of fibrotic diseases, in particular of scleroderma.

20 Claims, 9 Drawing Sheets

OTHER PUBLICATIONS

Shi-wen et al., "Scleroderma lung fibroblasts exhibit elevated and dysregulated type I collagen biosynthesis," Arthritis Rheum, 40:1237-1244 (1997).

Simonet et al., "Osteoprotegerin: a novel secreted protein involved in the regulation of bone density," Cell, 89:309-319 (1997).

Smith et al., "Production and function of murine macrophage inflammatory protein-1α in bleomycin-induced lung injury," J. Immunol., 153:4704-4712 (1994).

Wigley et al., "Novel therapy in the treatment of scleroderma," Exp. Opin. Invest. Drugs, 10(1):31-48 (2001).

Wigley et al., "The treatment of scleroderma," Curr. Opin. In Anti-inflam. & Immun. Invest. Drugs, 2:276-292 (2000).

Yano et al., "Synovial cells from a patient with rheumatoid arthritis produce osteoclastogenesis inhibitory factor/osteoprotegerin: reciprocal regulation of the production by inflammatory cytokines and basic fibroblast growth factor," J. Bone Miner Metab., 19:365-372 (2001).

Yasuda et al., "Identity of osteoclastogenesisis inhibitory factor (OCIF) and osteoprotegerin (OPG): a mechanism by which OPG/OCIF inhibits osteoclastogenesis in vitro," Endocrinology, 139:1329-1337 (1998).

Disthabanchong et al, "Regulation of bne cell development and function: implications from renal osteodystrophy", Journal of Investigative medicine. vol. 49, pp. 5117-5123, 1998.

Varga et al, "Systemic sclerosis: a prototypic multisystem fibrotic disorder", The Journal of Clinical Investigation, vol. 117, No. 3, pp. 557-567, 2003.

Wynn, "Common and unique mechanisms regulate fibrosis in various fibroproliferative diseases", The Journal of Clinical Investigation, vol. 117, No. 3, pp. 524-529, 2007.

Wynn, "Fibrotic disease and the Th1/Th2 paradigm" Nature Reviews Immunology. vol. 4, No. 8, pp. 583-594 (2004).

Yamaguchi et al, "Characterization of structural domains of himan osteoclastogenesis inhibitory factor", The Journal of Biological Chemistry, vol. 273, No. 9, pp. 5117-5123, 1998.

Auerbach, R., "Angiogenesis Assays: Problems and Pitfalls", Cancer and Metastasis Review, 19: pp. 167-172, 2000.

Berendsen, HJC, "A Glimpse of the Holy Grail", Science, 282: 642-643, 1998.

Gura T., "Cancer Models: Systems for Identifying New Drugs Are Often Faulty", Science, 278(5340): 1041-1042, enclosed pp. 1-6, 1997.

Jain, RK., "Barriers to Drug Delivery in Solid Tumors", Scientific American, pp. 58-65, 1994.

Rudinger, J. "Characteristics of the Amino Acids as Components of a Peptide Hormone Sequence", JA Parsons Ed., pp. 1-7, 1976.

Voet and Voet, "Biochemistry", Second Edition, John Wiley & Sons, Inc., pp. 235-241, 1995.

Beasley, DJ, et al., "Fibro-osseous lesions of the head and neck", The Journal of the Louisiana State Medical Society: Official Organ of the Louisiana State Medical Society, vol. 148(10), pp. 413-415, 1996.

Brown et al., "Fibrous Dysplasia of the Temporal Bone: Imaging Findings", Abstract, American Journal of Roentgenology, vol. 164, No. 3, pp. 679-682, 1995.

Lane et al., "Bisphosphonate Therapy in Fibrous Dysplasia", Abstract, Clinical Orthopaedics and Related Research, No. 382, pp. 6-12, 2001.

Mohammadi-Araghi et al., "Fibro-osseous Lesions of Craniofacial Bones", Abstract, The Role of Imaging. Radiologic Clinics of North America, vol. 13, No. 1, pp. 121-134, 1993.

Rosenblum et al., "Monostotic Fibrous Dysplasia of the Thoracic Spine", Abstract, Spine, vol. 12, No. 9, pp. 939-942, 1987.

* cited by examiner

USE OF OSTEOPROTEGERIN FOR THE TREATMENT AND/OR PREVENTION OF FIBROTIC DISEASE

FIELD OF THE INVENTION

The present invention is in the field of fibrotic diseases and connective tissue disorders. More specifically, the invention relates to the use of osteoprotegerin for the treatment and/or prevention of fibrotic diseases, in particular scleroderma. Combinations of osteoprotegerin with an interferon, a TNF antagonist or a further anti-fibrotic agent such as SARP-1 are also within the present invention.

BACKGROUND OF THE INVENTION

Fibrosis is a condition relating to an overproduction of collagen e.g. in the internal organs, including the kidneys, heart, lungs, stomach and joints.

Lung fibrosis is one of the predominant fibrotic diseases. Idiopathic Pulmonary Fibrosis (IPF) is characterized by chronic inflammation of the alveolar walls with progressive fibrosis, of unknown etiology. IPF, or cryptogenic fibrosing alveolitis, causes 50 to 60% of cases of idiopathic interstitial lung disease.

Usual interstitial pneumonia (UIP), a specific histopathologic pattern of interstitial pneumonia, is the classic pattern found on lung biopsy in IPF. At low magnification, the tissue appears heterogeneous, with alternating areas of normal lung, interstitial inflammation, fibrosis, and honeycombing. Interstitial inflammation consists of an alveolar septal infiltrate of lymphocytes, plasma cells, and histiocytes associated with hyperplasia of type II pneumocytes. The fibrotic zones are composed mainly of dense acellular collagen, although scattered foci of proliferating fibroblasts (fibroblastic foci), which are the sites of early and active disease, may also be seen, usually in an intra-alveolar location. Areas of honeycombing are composed of cystic fibrotic airspaces, frequently lined with bronchiolar epithelium and filled with mucus. Neutrophils may pool in the mucus. Smooth muscle hyperplasia often occurs in areas of fibrosis and honeycombing. The subpleural and paraseptal distribution, patchy character, and temporal heterogeneity are the most helpful features in identifying UIP.

An identical pattern of interstitial inflammation and fibrosis occurs in collagen vascular disorders (e.g., RA, SLE, progressive systemic sclerosis, mixed connective tissue disease, diabetes mellitus), pneumoconioses (e.g., asbestosis), radiation injury, and certain drug-induced lung diseases (e.g., by nitrofurantoin).

The clinical course of IPF is progressive; median survival is 4 to 6 yr after diagnosis. Prednisone is the usual treatment in case of IPF. Response to treatment is variable, but patients with earlier disease, at a more cellular stage before scarring predominates, appear more likely to improve with corticosteroid or cytotoxic therapy. Supportive and palliative treatment includes $O_2$ in high concentrations to relieve hypoxemia and, if bacterial infection occurs, antibiotics. Lung transplantation has been successful in patients with end-stage lung disease.

Fibrosis of the lung relates to an accumulation in the liver of connective tissue resulting from an imbalance between production and degradation of the extracellular matrix and accentuated by the collapse and condensation of preexisting fibers.

Liver fibrosis is a common response to hepatocellular necrosis or injury, which may be induced by a wide variety of agents, e.g., any process disturbing hepatic homeostasis (especially inflammation, toxic injury, or altered hepatic blood flow) and infections of the liver (viral, bacterial, fungal, and parasitic). Numerous storage disorders resulting from inborn errors of metabolism are often associated with fibrosis, including lipid abnormalities (Gaucher's disease); glycogen storage diseases (especially types III, IV, VI, IX, and X); $\alpha_1$-antitrypsin deficiency; storage of exogenous substances, as seen in iron-overload syndromes (hemochromatosis) and copper storage diseases (Wilson's disease); accumulation of toxic metabolites (as in tyrosinemia, fructosemia, and galactosemia); and peroxisomal disorders (Zellweger syndrome). Numerous chemicals and drugs cause fibrosis, especially alcohol, methotrexate, isoniazid, oxyphenisatin, methyldopa, chlorpromazine, tolbutamide, and amiodarone. Disturbances of hepatic circulation (eg, chronic heart failure, Budd-Chiari syndrome, veno-occlusive disease, portal vein thrombosis) and chronic obstruction to bile flow can lead to fibrosis. Lastly, congenital hepatic fibrosis is an autosomal recessive malformation.

The normal liver is made up of hepatocytes and sinusoids distributed within an extracellular matrix composed of collagen (predominantly types I, III, and IV) and noncollagen proteins, including glycoproteins (e.g., fibronectin, laminin) and several proteoglycans (e.g., heparan sulfate, chondroitin sulfate, dermatan sulfate, hyaluronate). Fibroblasts, normally found only in the portal tracts, can produce collagen, large glycoproteins, and proteoglycans.

Other liver cells (particularly hepatocytes and fat-storing Kupffer, and endothelial cells) also can produce extracellular matrix components. Fat-storing cells, located beneath the sinusoidal endothelium in the space of Disse, are precursors of fibroblasts, capable of proliferating and producing an excess of extracellular matrix. The development of fibrosis from active deposition of collagen is a consequence of liver cell injury, particularly necrosis, and inflammatory cells. The precise factors released from these cells is not known, but one or more cytokines or products of lipid peroxidation are likely. Kupffer cells and activated macrophages produce inflammatory cytokines. New fibroblasts form around necrotic liver cells; increased collagen synthesis leads to scarring. Fibrosis may derive from active fibrogenesis and from impaired degradation of normal or altered collagen. Fat-storing cells, Kupffer cells, and endothelial cells are important in the clearance of type I collagen, several proteoglycans, and denatured collagens. Changes in these cells' activities may modify the extent of fibrosis. For the histopathologist, fibrous tissue may become more apparent from passive collapse and condensation of preexisting fibers.

Thus, increased synthesis or reduced degradation of collagen results in active deposition of excessive connective tissue, which affects hepatic function: (1) Pericellular fibrosis impairs cellular nutrition and results in hepatocellular atrophy. (2) Within the space of Disse, fibrous tissue accumulates around the sinusoids and obstructs the free passage of substances from the blood to the hepatocytes. (3) Fibrosis around hepatic venules and the portal tracts disturbs hepatic blood flow. Venous resistance across the liver increases from portal vein branches to sinusoids and finally to hepatic veins. All three routes can be involved.

The fibrous bands that link portal tracts with central veins also promote anastomotic channels: Arterial blood, bypassing the normal hepatocytes, is shunted to efferent hepatic veins, which further impairs hepatic function and can accentuate hepatocellular necrosis. The extent to which these processes are present determines the magnitude of hepatic dysfunction: e.g., in congenital hepatic fibrosis, large fibrous bands involve predominantly the portal regions but usually spare the hepatic parenchyma. Congenital hepatic fibrosis thus presents as portal hypertension with preserved hepatocellular function.

Scleroderma is a disease of the connective tissue characterized by fibrosis of the skin and internal organs, leading to organ failure and death (Black et al., 1998; Clements and Furst, 1996). Scleroderma has a spectrum of manifestations and a variety of therapeutic implications. It comprises localized scleroderma, systemic sclerosis, scleroderma-like disorders, and Sine scleroderma (Smith, 2000). Whilst localized scleroderma is a rare dermatologic disease associated with fibrosis and manifestations limited to skin, systemic sclerosis is a multisystem disease with variable risk for internal organ involvement and variation in the extent of skin disease. Systemic sclerosis can be diffuse or limited. Limited systemic sclerosis is also called CREST (calcinosis, Raynaud's esophageal dysfunction, sclerodactyly, telangiectasiae). Scleroderma-like disorders are believed to be related to industrial environment exposure. In Sine disease, there is internal organ involvement without skin changes.

The major manifestations of scleroderma and in particular of systemic sclerosis are inappropriate excessive collagen synthesis and deposition, endothelial dysfunction, spasm, collapse and obliteration by fibrosis.

Scleroderma is a rare disease with a stable incidence of approximately 19 cases per 1 million persons. The cause of scleroderma is unknown. However, the genetic predisposition is important. Abnormalities involve autoimmunity and alteration of endothelial cell and fibroblast function. Indeed, systemic sclerosis is probably the most severe of the auto-immune diseases with a reported 50% mortality within 5 years of diagnosis (Silman, 1991).

In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

Several underlying biological processes are implicated in the initiation, severity and progression of the disease and include vascular dysfunction, endothelial cell activation and damage, leukocyte accumulation, auto-antibody production and crucially, an uncontrolled fibrotic response which may lead to death (Clements and Furst, 1996). Fibroblasts have a pivotal role in the pathogenesis of this disease. Primary fibroblasts obtained from patients with scleroderma exhibit many of the characteristic properties of the disease seen in vivo, notably increased extracellular matrix synthesis and deposition, notably of collagen and fibronectin, and altered growth factor and cytokine production such as of TGFβ and CTGF (Strehlow and Korn, 1998 and LeRoy, 1974).

There is no curative treatment of scleroderma. Innovative but high-risk therapy proposed autologous stem cell transplantation (Martini et al., 1999). In particular, there are currently no treatments for scleroderma targeting the fibrotic process (Wigley and Boling, 2000).

Identification of the genes associated with disease risk and scleroderma progression may lead to the development of effective strategies for intervention at various stages of the disease.

Osteoprotegerin (OPG) was first identified in 1997 as a novel cytokine secreted by fibroblasts (Simonet et al., 1997). Human OPG is a 401 amino acid protein and containing a signal peptide of 21 amino acids, that is cleaved before glutamic acid 22 giving rise to a 380 amino acid mature protein. Thus, OPG is a soluble protein. It is a member of the TNF receptor family (Morinaga et al., 1998, Yasuda et al., 1998), comprising four cysteine-rich TNFR like domains in its N-terminal portion (Simonet et al., 1997). OPG has been shown to have a role in the development of bone, and mice lacking the OPG gene had an osteoporotic phenotype and gross skeletal abnormalities (Min et al., 2000).

Osteoprotegerin, which is produced by osteoblasts and bone marrow stromal cells, lacks a transmembrane domain and acts as a secreted decoy receptor which has no direct signaling capacity. OPG acts by binding to its natural ligand osteoprotegerin ligand (OPGL), which is also known as RANKL (receptor activator of NF-kappaB ligand). The binding between OPG and OPGL binding prevents OPGL from activating its cognate receptor RANK, which is the osteoclast receptor vital for osteoclast differentiation, activation and survival.

Human OPG is member of the TNFR family and is a single-copy gene that consists of 5 exons and spans 29 kb of the genome (Simonet et al., 1997). Recombinant OPG exists in monomeric and dimeric forms of apparent molecular weights of 55 and 110 kDa, respectively (Simonet et al., 1997). Truncation of the N-terminal domain to cysteine 185 produces inactivation, presumably by disruption of the SS3 disulfide bond of the TNFR-like domain, whereas truncation of the C-terminal portion of the protein to amino acid 194 did not alter biological activity. Thus, the N-terminal TNFR-like domain of OPG is sufficient to prevent osteoclastogenesis (Simonet et al., 1997).

Overexpression of OPG in transgenic mice leads to profound osteopetrosis secondary to a near total lack of osteoclasts. Conversely, ablation of the OPG gene causes severe osteoporosis in mice. Ablation of OPGL or RANK also produces profound osteopetrosis, indicating the important physiological role of these proteins in regulating bone resorption. The secretion of OPG and OPGL from osteoblasts and stromal cells is regulated by numerous hormones and cytokines, often in a reciprocal manner. The relative levels of OPG and OPGL production are thought to ultimately dictate the extent of bone resorption. Excess OPGL increases bone resorption, whereas excess OPG inhibits resorption. Recombinant OPG blocks the effects of virtually all factors, which stimulate osteoclasts, in vitro and in vivo. OPG also inhibits bone resorption in a variety of animal disease models, including ovariectomy-induced osteoporosis, humoral hypercalcemia of malignancy, and experimental bone metastasis. Therefore, OPG might represent an effective therapeutic option for diseases associated with excessive osteoclast activity (Kostenuik and Shalhoub, 2001).

However, osteoprotegerin has not yet been suggested to be involved in fibrotic diseases.

SUMMARY OF THE INVENTION

The invention is based on the finding that administration of osteoprotegerin results in a significant amelioration of the disease in an established animal model of lung fibrosis. Lung fibrosis is one of the manifestations of scleroderma It is therefore a first object of the invention to use osteoprotegerin for the preparation of a medicament for the treatment and/or prevention of fibrotic diseases, in particular of scleroderma. It is a second object of the invention to use a cell expressing osteoprotegerin, or an expression vector comprising the coding sequence of osteoprotegerin, for the preparation of a medicament for the treatment and/or prevention of a fibrotic disease, in particular systemic sclerosis. Pharmaceutical compositions comprising osteoprotegerin and further anti-fibrotic drugs, such as halofuginone, and methods of treatment comprising administering osteoprotegerin to the human body are also within the scope of the present invention.

DESCRIPTION OF THE INVENTION

Figure 1:
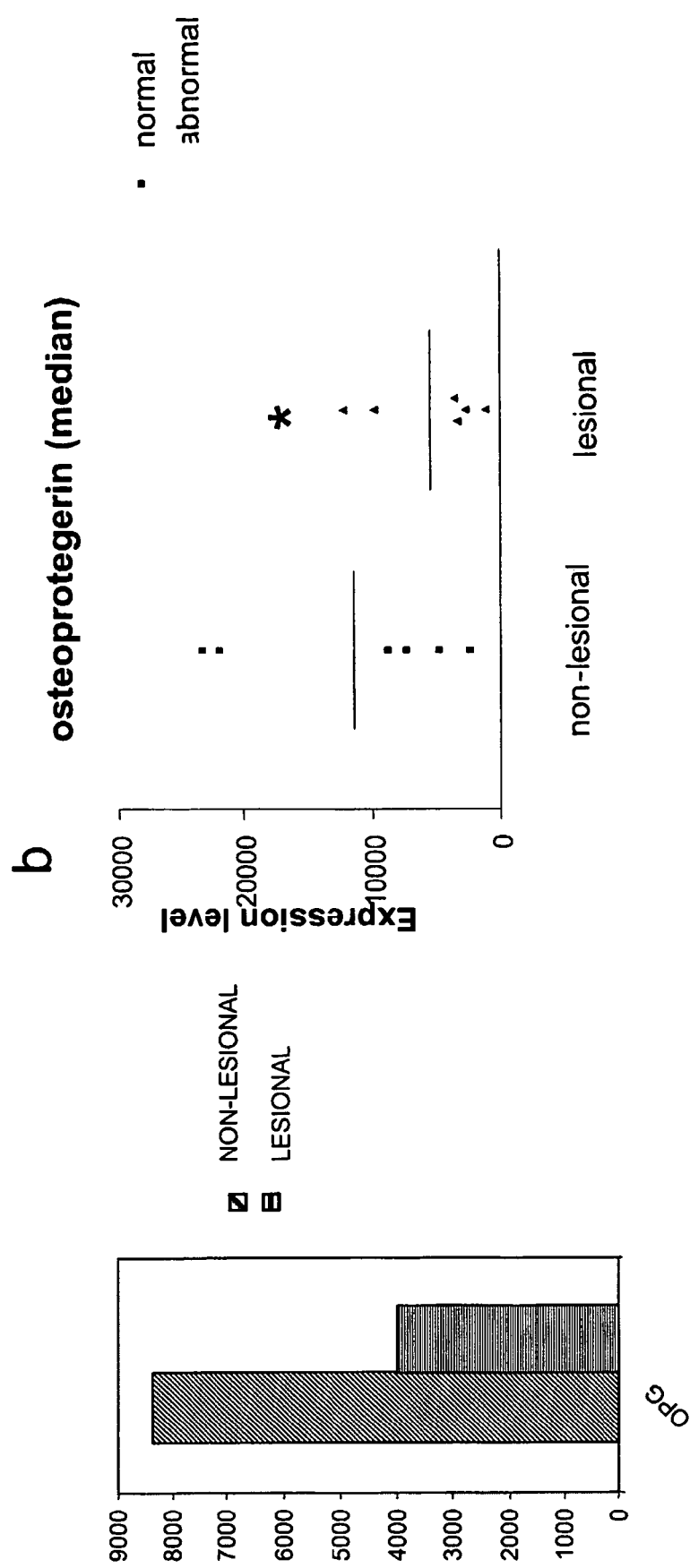
FIG. 1 Expression of OPG mRNA in normal (hatched) and diseased (hatched horizontally) fibroblasts from 6 scleroderma patients determined by gene filter microarray analysis. The mean expression level is given in (a) and the median is given in (b).

In accordance with the present invention, DNA gene filter microarray technology was used to identify differentially expressed genes in skin fibroblasts from fibrotic lesions obtained from patients with systemic sclerosis (scleroderma) compared to normal skin fibroblasts from the same patients. One gene, which was consistently down regulated in the scleroderma fibroblasts, was osteoprotegerin (OPG), also called osteoclastogenesis inhibitory factor. Abnormal fibroblasts expressed significantly lower levels OPG mRNA compared to normal fibroblasts in 7 out of 9 patients tested. These results were corroborated by real time PCR analysis. In addition, real time RT-PCR analysis of total RNA isolated from whole biopsy specimens of abnormal skin from scleroderma patients indicated lower levels of OPG mRNA compared to clinically normal, age, sex and anatomical site matched control biopsies. OPG protein was also decreased in lesional fibroblasts compared to normal fibroblasts isolated from the same patients. In vitro, OPG is able to decrease TGFβ mediated collagen synthesis following transfection of fibroblasts with OPG cDNA or following treatment with the recombinant protein. A further in vitro activity of OPG is to inhibit TGFβ induced connective tissue growth factor (CTGF) expression. CTGF normally induces sythesis of extracellular matrix components in fibroblasts.

These in vitro data were further supported by in vivo data in an established animal model. Administration of osteoprotegerin reduced lung fibrosis and decreased collagen deposition in the bleomycin-induced lung fibrosis model. At the histological level, the lungs of osteoprotegerin treated animals resembled those of naïve, untreated mice.

Therefore, the invention relates to the use of a substance for the manufacture of a medicament for the treatment and/or prevention of a fibrotic disease, wherein the substance is selected from the group consisting of:

a) A polypeptide comprising SEQ ID NO: 2 or SEQ ID NO: 4;

b) A polypeptide comprising amino acids 22 to 401 of SEQ ID NO: 2 or SEQ ID NO: 4;

c) A polypeptide comprising one, two, three or four cysteine-rich domains of osteoprotegerin;

d) A polypeptide comprising amino acids 22 to 194 of SEQ ID NO: 2 or SEQ ID NO: 4;

e) A mutein of any of (a) to (d), wherein the amino acid sequence has at least 40% or 50% or 60% or 70% or 80% or 90% identity to at least one of the sequences in (a) to (d);

f) A mutein of any of (a) to (d) which is encoded by a DNA sequence which hybridizes t the complement of the DNA sequence encoding any of (a) to (d) under moderatel stringent conditions or under highly stringent conditions;

g) A mutein of any of (a) to (d) wherein any changes in the amino acid sequence ar conservative amino acid substitutions to the amino acid sequences in (a) to (d);

h) a salt or an isoform, fused protein, functional derivative, active fraction or circularly permutated derivative of any of (a) to (g).

It will be appreciated by the person skilled in the art that in accordance with the present invention, a substance which stimulates release or potentiates the activity of endogenous osteoprotegerin can equally be used for treatment and/or prevention of fibrotic disease, in particular of scleroderma. Said substance may be mature osteoprotegerin itself, or any fragment of osteoprotegerin binding to OPGL and thereby preventing OPGL binding to RANK, and preventing initiating signaling through RANK. Such a substance may be e.g. an antibody directed to OPGL. It is known that OPG binds to OPGL, and that this interaction prevents binding of OPGL to its receptor RANK. Therefore, the person skilled in the art will appreciate that any substance preventing the binding of OPGL to its receptor RANK, or any other agent blocking RANK activity or signalling, will have the same activity as osteoprotegerin in prevention and/or treatment of fibrotic disease, in particular of scleroderma. Agents blocking OPGL binding to RANK may be antagonistic antibodies directed to OPGL, for instance. Agents blocking RANK activity may further be antagonistic antibodies directed to RANK, for instance. Further agents blocking OPGL/RANK interaction may be chemical compounds interfering with binding of these two proteins to each other, for example, but also any other chemical or biological inhibitor of signalling through the RANK receptor.

The full length cDNA of human osteoprotegerin has been cloned and is depicted as SEQ ID NO: 1 of the attached sequence listing. The corresponding amino acid sequence is given as SEQ ID NO: 2 of the attached sequence listing. The sequences are described at www.ncbi.nim.nih.gov under AB_008821, as well as by Morinaga et al. (1998). An isoform or polymorphic form of osteoprotegerin has been described by Simonet et al. (1997). The cDNA according to Simonet et al. (1997) is depicted as SEQ ID NO: 3 of the attached sequence listing, and the corresponding amino acid sequence is given as SEQ ID NO: 4. Both sequences are further available from www.ncbi.nlm.nih.gov under U94332. The only difference between the proteins found by Morinaga et al. and Simonet et al. concerns amino acid position 263, which may be an aspartic acid or an alanine, respectively.

The term "osteoprotegerin", as used herein, relates to any of the substances considered above in (a) to (h).

The term "treatment and/or prevention" as used herein encompasses any attenuation, reduction, or partial, substantial or complete prevention or blockage of disease formation, development, progression or of the formation, development or progression of any one or several or all of the symptoms of the disease.

The term "fibrotic disease" as used herein relates to diseases involving fibrosis, which may e.g. be due to chronic inflammation or repair and reorganization of tissues. Fibrosis may involve any organ of the human body, such as e.g. the skin, lung, pancreas, liver or kidney. Therefore, the invention also relates to treatment and/or prevention of fibrotic diseases such as liver cirrhosis, interstitial pulmonary fibrosis, Dupuytren's contracture, keloid and other scarring/wound healing abnormalities, postoperative adhesions and reactive fibrosis, as well as chronic heart failure, in particular after myocardial infarction. Further diseases or disorders treatable with osteoprotegerin comprise wound-healing diseases, in particular wound healing in the lung, comprising chronic inflammation of the lung and ultimately fibrosis or scarring of lung surfaces. Disorders involving inflammation of the lung comprise e.g. idiopathic pulmonary fibrosis, sarcoidosis, bronchopulmonary dysplasia, fibroproliferative ARDS, as well as pulmonary manifestations or systemic diseases such as rheumatoid arthritis (Krein et al., 2001).

Fibrosis generally involves generation or proliferation of connective tissue, which replaces functional specialized tissue of a given organ. Therefore, in a preferred embodiment of the present invention, the fibrotic disease is a connective tissue disease.

In a preferred embodiment, the fibrotic disease is scleroderma.

The term "scleroderma" as used herein relates to a disease also called systemic sclerosis or systemic scleroderma. These terms are used synonymously within the present patent application. Systemic sclerosis is a chronic disease of unknown cause, characterized by diffuse fibrosis; degenerative changes; and vascular abnormalities in the skin, articular structures, and internal organs (especially the esophagus, gastrointestinal tract, lung, heart, and kidney, for example). It may be localized, or mixed, systemic, limited or diffuse.

The term "scleroderma" preferably relates to localized, systemic, limited and diffuse scleroderma as well as overlap syndromes.

Localized scleroderma primarily affects the skin, but may also affect the underlying muscles and bones. However, it generally does not affect internal organs. Localized scleroderma is relatively mild, and may be related to systemic scleroderma in terms of similar superficial symptoms, such as the appearance of skin biopsy under the microscope.

Systemic scleroderma comprises several types of symptoms or groups of symptoms, such as CREST, limited and diffuse. It may also be referred to as progressive systemic sclerosis, or familial progressive systemic sclerosis. Systemic scleroderma may e.g. affect the skin, blood vessels, and/or internal organs. When it affects the skin, it can cause the skin to harden, most commonly on the hands and/or face. When it affects the blood vessels, it can cause Raynaud's disease. The most serious forms of systemic sclerosis affect the internal organs, and may cause disability or even death. Among others, systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system. With regard to the nervous system abnormalities, carpal tunnel syndrome followed by trigeminal neuralgia are the most common.

Limited Scleroderma may e.g. be limited to the hands, although the face and neck may also be involved.

Diffuse Scleroderma comprises skin tightening and also occurs above the wrists (or elbows). There are several sub-categories of diffuse systemic sclerosis, such as "scleroderma sine scleroderma" where there is internal organ fibrosis, but no skin tightening; and familial progressive systemic sclerosis, a rare form occurring in families.

Overlap syndromes are referred to if a scleroderma patient also has other autoimmune disease (such as lupus, rheumatoid arthritis, etc.), as e.g. in diffuse scleroderma in overlap with lupus. Scleroderma symptoms can also be a part of mixed connective tissue disease (MCTD), or Undifferentiated Connective Tissue Disease (UCTD).

The term "osteoprotegerin" as used herein, relates to a protein comprising all, or a portion of the sequence of SEQ ID NO: 2 or 4 (both human) of the enclosed sequence listing, as well as to salts, isoforms, muteins, active fractions, functional derivatives and circularly permutated derivatives thereof.

OPG from species other than human, such as mouse or rat, may be used in accordance with the present invention, as long as there is a sufficient identity between the proteins as to allow the protein to exhibit its biological activity, and without eliciting a substantial immune response in a human being.

Preferably, the term "osteoprotegerin" refers to a mature protein lacking the signal peptide. The signal peptide comprises the N-terminal 21 amino acids of OPG as defined in SEQ ID NO: 2 or 4, i.e. the mature protein comprises amino acids 22 to 401 of SEQ ID NO: 2 or 4. The term "osteoprotegerin", as used herein, further relates to any fragment, portion, domain or sub-domain of SEQ ID NO: 2 or 4 showing the desired activity in scleroderma or other fibrotic diseases. Protein fragments, isoforms, differentially glycosylated or sialylated forms or one or more domains of the protein may be used according to the invention, as long as they exhibit any beneficial effect on fibrotic disease, preferably an effect which is at least comparable of the full length protein. The beneficial effect can be measured in one of the in vitro or in vivo tests described in the examples below, or in any other assay adequate to demonstrate an effect in fibrotic diseases, in particular of scleroderma.

For example, osteoprotegerin comprises a cysteine-rich TNFR-like domain in its N-terminal portion, as described by Simonet et al., 1997. A fragment comprising this domain was shown to retain the biological activity of OPG in an in vitro test. Therefore, a preferred OPG fragment comprises the TNFR-like domain of OPG, in particular a fragment comprising amino acids 22 to 194 of SEQ ID NO: 2 or 4.

In accordance with the present invention, osteoprotegerin can be a naturally occurring, i.e. native protein, or a recombinant protein. Recombinant production may be carried out in eukaryotic cells, such as yeast cells or mammalian cells, preferably in CHO cells, HEK cells (human embryonic kidney cells) or in human fibroblast cells or cell lines. It may further be produced in prokaryotic cells such as E. coli.

Osteoprotegerin has been described to occur in monomeric and dimeric form (Simonet et al., 1997). Therefore, in accordance with the present invention, OPG may be a monomer, a dimer or a multimer.

Preferably, osteoprotegerin is glycosylated at one or more sites. It may also be unglycosylated, depending on the given needs and the source of production or isolation of the protein.

The term "salts" herein refers to both salts of carboxyl groups and to acid addition salts of amino groups of osteoprotegerin molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of osteoprotegerin relevant to the present invention, i.e., exert a beneficial effect on fibrotic diseases, in particular scleroderma.

Isoforms or splice variants of osteoprotegerin may also be used according to the invention, as long as they are capable of inhibiting disease progression and/or symptoms of that disease.

As used herein the term "muteins" refers to analogs of osteoprotegerin, in which one or more of the amino acid residues of natural osteoprotegerin are replaced by different amino acid residues, or are deleted, or one or more amino acid residues are added to the natural sequence of osteoprotegerin, having preferably at least the same activity as wild type osteoprotegerin or even having a much more potent activity. The biological activity of OPG can e.g. be measured by assaying the binding of OPG to its natural ligand OPGL. Assays for assessing protein-protein interactions are well known by the person skilled in the art. Examples for such assays are ELISA type binding assays, immuno-precipitation assays, or measurement in any other suitable system such as the BIAcore system. These muteins are prepared by known synthesis and/or by site-directed mutagenesis techniques, or any other known technique suitable therefor.

Any such mutein preferably has a sequence of amino acids sufficiently duplicative of that of mature osteoprotegerin, such as to have at least a substantially similar activity of osteoprotegerin. The activity of a osteoprotegerin mutant can further be tested in the assays explained in the examples below. Measuring the amount of collagen synthesis in fibroblasts treated with OPG may a suitable test for assessing the activity of osteoprotegerin muteins, for example.

Muteins in accordance with the present invention include proteins encoded by a nucleic acid, such as DNA or RNA, which hybridizes to DNA or RNA, which encodes osteoprotegerin, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al.(Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of osteoprotegerin, such as to have substantially similar, or even better, biological activity as osteoprotegerin.

One easily measurable activity of osteoprotegerin is its capability of reducing collagen synthesis. As long as the mutein has substantial collagen reducing activity, it can be considered to have substantially similar activity to osteoprotegerin. Thus, it can be determined whether any given mutein has at least substantially the same activity as osteoprotegerin by means of routine experimentation comprising subjecting such a mutein.

In a preferred embodiment, any such mutein has at least 40% identity or homology with the sequence of mature osteoprotegerin. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al, 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of osteoprotegerin, which can be used in accordance with the present invention, or nucleic acids coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of osteoprotegerin polypeptides or proteins, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |

TABLE I-continued

Preferred Groups of Synonymous Amino Acids

| Amino Acid | Synonymous Group |
|---|---|
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of osteoprotegerin polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fused protein" refers to a polypeptide comprising osteoprotegerin, or a mutein thereof, fused with another protein, which, e.g., has an extended residence time in body fluids. Fusion proteins comprising all or a functional part of osteoprotegerin fused to all or a functional part of a protein capable of improving the biological activities of the molecule, like half-life in the human body, for instance, are preferred according to the invention. In a preferred embodiment the fused protein comprises an immunoglobulin (Ig) fusion. Fusion proteins comprising all or part of osteoprotegerin fused to all or part of an immunoglobulin are highly preferred. They can be monomeric or multimeric, hetero- or homomultimeric. Advantageously, the fused protein comprises the constant region of an immunoglobulin, in particular of the Fc portion of the immunoglobulin. Embodiments in which the immunoglobulin is of the IgG1 or IgG2 isotype are further preferred according to the invention. Preferably, the fusion is an Fc fusion.

Osteoprotegerin may thus be fused to another protein, polypeptide or the like, e.g., an immunoglobulin or a fragment thereof. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 13) introduced between the osteoprotegerin sequence and the immunoglobulin sequence.

"Functional derivatives" as used herein cover derivatives of osteoprotegerin, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is at least substantially similar to the activity of osteoprotegerin, and do not confer toxic properties on compositions containing it. Therefore, in a preferred embodiment the functional derivative comprises at least one moiety attached to one or more functional groups, which occur as one or more side chains on the amino acid residues.

In accordance with the present invention, polyethylene glycol (PEG) side-chains are highly preferred moieties. PEG side chains may mask antigenic sites and extend the residence of the substance they are attached to in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

"Active fractions" of osteoprotegerin and its muteins and fused proteins, cover any fragment or precursors of the polypeptide chain of the protein molecule alone or together with associated molecules or residues linked thereto, e.g., sugar or phosphate residues, or aggregates of the protein molecule or the sugar residues by themselves, provided said active fraction has at least a substantially similar activity to osteoprotegerin.

The invention further relates to the use of a nucleic acid molecule for manufacture of a medicament for the treatment and/or prevention of scleroderma, wherein the nucleic acid molecule comprises a nucleic acid sequence encoding a polypeptide comprising an amino acid sequence selected from the group consisting of:

a) A polypeptide comprising SEQ ID NO: 2 or SEQ ID NO: 4;

b) A polypeptide comprising amino acids 22 to 401 of SEQ ID NO: 2 or SEQ ID NO: 4;

c) A polypeptide comprising one, two, three or four cysteine-rich domains of osteoprotegerin;

d) A polypeptide comprising amino acids 22 to 194 of SEQ ID NO: 2 or SEQ ID NO: 4;

e) A mutein of any of (a) to (d), wherein the amino acid sequence has at least 40% or 50% or 60% or 70% or 80% or 90% identity to at least one of the sequences in (a) to (d);

f) A mutein of any of (a) to (d) which is encoded by a DNA sequence which hybridizes to the complement of the native DNA sequence encoding any of (a) to (d) under moderately stringent conditions or under highly stringent conditions;

g) A mutein of any of (a) to (d) wherein any changes in the amino acid sequence are conservative amino acid substitutions to the amino acid sequences in (a) to (d);

h) An isoform, fused protein or active fraction of any of (a) to (g).

for the manufacture of a medicament for the treatment and/or prevention of fibrotic diseases. The invention preferably relates to the use of said nucleic acid molecules for the treatment and/or prevention of connective tissue diseases, and in particular of scleroderma.

In accordance with the present invention, osteoprotegerin may also be administered to the human body in form of a vector comprising said nucleic acid molecule. Therefore, the invention further relates to the use of a vector comprising said nucleic acid molecule for the manufacture of a medicament for the treatment and/or prevention of scleroderma or another fibrotic disorder Preferably, the vector is an expression vector, comprising a promoter operably linked to all or part of the coding sequence of osteoprotegerin. In a further preferred embodiment, the vector is a gene therapy vector. Gene therapy vectors are known in the art, most of them are virally derived vectors, such as adenoviral or lentiviral vectors.

According to the invention, osteoprotegerin may also be administered to the human body in form of a cell producing and/or secreting osteoprotegerin. Therefore, the invention further relates to the use of a cell expressing osteoprotegerin for the manufacture of a medicament for the treatment and/or prevention of scleroderma or any other fibrotic disease, i.e. to cell therapy for the treatment and/or prevention of scleroderma or other fibrotic diseases. The cell may be a naturally producing osteoprotegerin and/or a transfected cell that produces recombinant osteoprotegerin. Preferred are cells expressing and secreting high amounts of the protein, such as over-expressing cells carrying high copy numbers of an expression vector comprising a nucleic acid molecule encoding osteoprotegerin.

As fibroblasts represent the machinery of fibrosis they are the most suitable cells for anti-fibrotic and scleroderma therapy. Therefore, preferably, osteoprotegerin expressing fibroblasts are used in accordance with the present invention.

The invention further relates to a cell comprising a vector comprising a nucleic acid molecule encoding all or part of osteoprotegerin for the preparation of a medicament for treatment and/or prevention of fibrotic disease, in particular of scleroderma. A cell that has been genetically modified to produce a polypeptide according to the invention is also within the scope of the present invention.

The use of an expression vector for inducing and/or enhancing the endogenous production of osteoprotegerin in a cell normally silent or expressing amounts of the inhibitor which are not sufficient, are also contemplated according to the invention. Thus, the invention makes use of a technology known as endogenous gene activation (EGA) for the production of the desired protein.

Several combined treatments are preferred in accordance with the present invention. Therefore, preferably, the medicament of the invention further comprises:

Interferon, in particular interferon-β

A Tumor Necrosis Factor (TNF) antagonist, in particular soluble TNFRs, such as soluble p55 (TBPI) and/or soluble p75 (TBP II);

A further anti-scleroderma agent;

An anti-scleroderma agent selected from the group consisting of Halofuginone, ACE inhibitors, calcium channel blockers, proton pump inhibitors, NSAIDs, COX-inhibitors, corticosteroids, tetracycline, pentoxifylline, bucillamine, geranylgeranyl transferase inhibitors, rotterlin, prolyl-4-hydroxlase inhibitors, c-proteinase inhibitors, lysyl-oxidase inhibitors, relaxin, halofugi-none, prostaglandins, prostacyclins, endothelin-1, nitric oxide, angiotensin II inhibitors, anti-oxidants, or SAPR-1.

SARP-1 is a protein shown to have a beneficial effect in fibrotic diseases such as scleroderma (WO02/46225). Fragments, isoforms, active fractions, fused proteins or functional derivatives of SARP-1, as described in WO02/46225, may also be used in combination with osteoprotegerin, in accordance with the present invention.

All treatments are intended for simultaneous, sequential or separate use.

Pharmaceutical compositions comprising one or more of the above substances, together with osteoprotegerin, are within the scope of the present invention.

Although there is presently no cure for scleroderma, several agents or treatments are presently being used to treat scleroderma symptoms. Such anti-scleroderma agents, which may be used as combination therapy according to the invention, are summarized e.g. in Leighton (2001) or Wigley and Sule (2001), which are fully incorporated by reference herein.

Interferons are predominantly known for inhibitory effects on viral replication and cellular proliferation. Interferon-γ, for example, plays an important role in promoting immune and inflammatory responses. Interferon β (IFN-β, an interferon type I), is said to play an anti-inflammatory role.

In yet a further embodiment of the invention, osteoprotegerin is used in combination with a TNF antagonist. TNF antagonists exert their activity in several ways. First, antagonists can bind to or sequester the TNF molecule itself with sufficient affinity and specificity to partially or substantially neutralise the TNF epitope or epitopes responsible for TNF receptor binding (hereinafter termed "sequestering antagonists"). A sequestering antagonist may be, for example, an antibody directed against TNF.

Alternatively, TNF antagonists can inhibit the TNF signalling pathway activated by the cell surface receptor after TNF binding (hereinafter termed "signalling antagonists"). TNF antagonists are easily identified and evaluated by routine screening of candidates for their effect on the activity of native TNF on susceptible cell lines in vitro, for example human B cells, in which TNF causes proliferation and immunoglobulin secretion. The assay contains TNF formulation at varying dilutions of candidate antagonist, e.g. from 0.1 to 100 times the molar amount of TNF used in the assay, and controls with no TNF or only antagonist (Tucci et al., 1992).

Sequestering antagonists are the preferred TNF antagonists to be used according to the present invention. Amongst sequestering antagonists, those polypeptides that bind TNF with high affinity and possess low immunogenicity are preferred. Soluble TNF receptor molecules and neutralising antibodies to TNF are particularly preferred. For example, soluble forms of TNF-RI (p55) and TNF-RII (p75) are useful in the present invention. Truncated forms of these receptors, comprising the extracellular domains of the receptors or functional portions thereof, are more particularly preferred antagonists according to the present invention. Truncated soluble TNF type-I and type-II receptors are described in EP914431, for example.

Truncated forms of the TNF receptors are soluble and have been detected in urine and serum as about 30 kDa or 40 kDa TNF inhibitory binding proteins, which are called TBPI and TBPII, respectively (Engelmann et al., 1990). The simultaneous, sequential, or separate use of osteoprotegerin with the TNF antagonist and/or an Interferon is preferred, according to the invention.

According to the invention, TBPI and TBPII are preferred TNF antagonists to be used in combination with an osteoprotegerin. Derivatives, fragments, regions and biologically active portions of the receptor molecules functionally resemble the receptor molecules that can also be used in the present invention. Such biologically active equivalent or derivative of the receptor molecule refers to the portion of the polypeptide, or of the sequence encoding the receptor molecule, that is of sufficient size and able to bind TNF with such an affinity that the interaction with the membrane-bound TNF receptor is inhibited or blocked.

In a further preferred embodiment, human soluble TNF-RI (TBPI) is the TNF antagonist to be used according to the invention. The natural and recombinant soluble TNF receptor molecules and methods of their production have been described in the European Patents EP 308 378, EP 398 327 and EP 433 900.

Whilst it may be beneficial to block TNF-α in early stages of the disease, it has been discussed that in later stages, TNF itself may exert a beneficial effect on scleroderma (Abraham et al., 2000). Therefore, the invention further relates to a combination of osteoprotegerin and TNF for treatment or prevention of scleroderma, in particular in advanced stages of disease. TNF-α or TNF-β may be used in accordance with the invention.

The invention further relates to a pharmaceutical composition comprising osteoprotegerin, optionally together with one or more pharmaceutically acceptable carriers, diluents or excipients, for the treatment and/or prevention of fibrotic disease, in particular scleroderma. The pharmaceutical composition may further comprise any of the above-identified further components, and in particular an interferon, a TBP or a COX inhibitor.

The pharmaceutical composition according to the invention may also comprise a vector comprising a nucleic acid molecule according to the invention, or a cell expressing osteoprotegerin.

The active ingredients of the pharmaceutical, i.e. polypeptides, nucleic acids or cells according to the invention, or combinations thereof, as well as the combinations of substances mentioned above, may be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amount of the active protein(s) will be a function of many variables, including the type of receptor, the affinity of the substance according to the invention to its receptor, any residual cytotoxic activity exhibited thereby, the route of administration, the clinical condition of the patient.

A "therapeutically effective amount" is such that when administered, the substance according to the invention results in a beneficial effect on disease development or progression in vivo. The dosage administered, as single or multiple doses, to an individual will vary depending upon a variety of factors, including the pharmacokinetic properties of OPG, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art.

The dose of the polypeptide according to the invention required will vary from about 0.0001 to 100 mg/kg or about 0.01 to 10 mg/kg or about 0.1 to 5 mg/kg or about 1 to 3 mg/kg, although as noted above this will be subject to a great deal of therapeutic discretion. The medicament of the invention may be administered daily, every other day, or three times per week.

The daily doses are usually given in divided doses or in sustained release form effective to obtain the desired results. Second or subsequent administrations can be performed at a dosage, which is the same, less than or greater than the initial or previous dose administered to the individual. A second or subsequent administration can be administered during or prior to onset of the disease.

The invention further relates to a method for treating and/or preventing fibrotic diseases, in particular scleroderma, comprising administering to a patient in need thereof an effective amount of a substance according to the invention, optionally together with a pharmaceutically acceptable carrier. Alternatively, or additionally, a cell producing osteoprotegerin or a nucleic acid molecule of the invention, optionally comprised in an expression vector, may be administered according to the invention.

The expression vector may be administered systemically. Preferably the expression vector is administered by intramuscular injection. A further preferred route of administration is inhalation, in particular if lung fibrosis is involved in the disease. Topical administration of an expression vector comprising OPG sequences, or of an OPG polypeptide according to the invention, is a further preferred route of administration, in particular if there is an involvement of the skin.

The invention further relates to a method for the preparation of a pharmaceutical composition comprising admixing an effective amount of osteoprotegerin with a pharmaceutically acceptable carrier, and to a method of treatment and/or prevention of arthritis comprising administering to a host in need thereof an effective inhibiting amount of osteoprotegerin.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Methods

Patient Samples

Two mm$^3$ punch biopsies were taken from lesional or non-lesional skin (usually from forearm skin) of nine age and sex matched patients with diffuse cutaneous systemic sclerosis (SSc). All patients fulfilled the criteria of the American College of Rheumatology for the diagnosis of SSc.

Fibroblast Cultures

Fibroblasts were obtained from the biopsies by in vitro culture as previously described (Abraham et al., 1991). Briefly, biopsies were cut into pieces and placed in sterile plastic dishes or flasks. After 15 minutes of drying at room temperature the pieces of biopsy were adherent to the tissue culture plastic and were then cultured in fibroblast growth medium (FGM) consisting of Dulbecco's modified Eagle's medium (DMEM) containing 10% fetal calf serum (FCS), 2 mM L-glutamine, 1 mM sodium pyruvate, 100 units per ml penicillin, 100 µg per ml streptomycin, 50 µg per ml gentamicin and 2.5 µg per ml amphotericin B. After 2-3 weeks of incubation in a humidified atmosphere of 5% $CO_2$ in air, the fibroblast outgrowths were detached by brief trypsinisation and re-cultured in FGM without gentamicin and amphotericin B. In experiments, fibroblasts were used between passages 2 and 5. The fibroblast phenotype was confirmed by their typical morphology in monolayer and three-dimensional collagen gel cultures.

RNA Isolation

Total RNA was isolated from confluent scleroderma fibroblasts in early passage using Trizol (Life Technologies) according to the manufacturer's protocol. The final RNA pellet was resuspended in sterile DEPC treated water at a concentration of 1 µg/µl and stored at −80° C.

cDNA Probe Synthesis

Two µg total RNA was mixed with 1.3 µl of cytokine specific primers (R&D systems cat. no. GAC11) and incubated at 70 C for 2 min a 0.5 ml eppendorf tube. The tubes were then cooled to 50° C. for 2 min after which time reaction mixture containing 2 µl of 5× reaction buffer (250 mM Tris-HCl pH 8.3, 375 mM KCl and 15 mM $MgCl_2$), 1 µl of 10×dNTP mixture (5 mM dGTP, 5 mM dCTP and 5 mM dTTP), 3.5 µl of $\alpha^{32}$P-dATP (3000 Ci/mmol, Amersham cat. no. PB10204), 0.5 µl DTT (100 mM) and 1 µl of superscript II (Life Technologies) were added. The reaction mixture was mixed briefly by pipetting and incubated at 50 C for 25 min. The reaction was stopped by addition of 1 µl of 0.1 M EDTA pH 8.0 containing 1 mg/ml glycogen). The labeled cDNA was then purified from un-incorporated deoxynucleotides using a Chromaspin-200 DEPC-$H_2$O column (Clontech) according to the manufacturer's instructions. cDNA containing fractions were identified by Czerenkov counting. The peak fraction (normally fraction 2 out of a total of 6 collected) was treated with 0.1 volumes of 1 M NaOH containing 1 mM EDTA for 20 min at 70 C to hydrolyze the RNA, and then neutralized with an equal volume of 1 M $NaH_2PO_4$ containing 2.5 µg of human Cot-1 DNA (Life Technologies) for 20 min at 70° C. The heat treated neutralized cDNA probe was then added directly to the hybridization mixture.

Hybridization to Gene Filter Microarrays

Gene filter microarrays (human cytokine expression array, R&D systems cat no. GA001) were prehybridized at 68° C. for 2 h in 5 ml of Express Hybridization solution (Clontech) containing 0.5 µg/ml salmon sperm DNA (Life technologies) in roller bottles, in a Hybaid hybridization oven (MWG Biotech). After this time the prehybrization solution was replaced with fresh hybridization solution containing the cDNA probe preparation at a specific activity of between 0.25 to 1×10$^6$ cpm/ml. Hybridization was for 16-20 h at 68 C. After hybridization, filters were washed 4 times with 2×SSC/1% SDS at 68 C for 20 minutes perwash and twice with 0.1×SSC/0.5% SDS for 15 min per wash. Filters were then sealed in Saran wrap™ and exposed to a K-type storage phosphor imaging screen (Biorad) for varying times (4 h to 4 days) at room temperature.

Image Analysis

Imaging screens were scanned at a resolution of 50 µm using a Biorad Personal FX phosphoimager. The resultant 16 bit digital file was converted to TIF format and the image analyzed using Arrayvision software (Imaging Research Inc.) For each sample, we measured the pixel intensity of the 384 genes spotted in duplicate on the filter. The background signal was subtracted and an average pixel intensity for each pair of spots in the array was generated (=expression level).

Confirmation of Microarray Results on Selected Genes by RT-PCR.

One µg of total RNA from each patient sample was reverse transcribed using an oligo dT primer (Promega) in a 20 µl reaction volume containing 5 mM $MgCl_2$, 10 mM Tris-HCl, 50 mM KCl, 0.1% Triton X-100, 1 mM each of dATP, dGTP, dCTP, dTTP, 0.5 units recombinant RNasin ribonuclease inhibitor (Promega) and 15 units AMV reverse transcriptase (Promega). The reaction mixture was incubated at 42 C for 60 min, heated at 95 C for 5 min then diluted to 200 µl with sterile water. Dilutions of the reverse transcriptase reaction were then subjected to real time PCR analysis on a Taqman (PE Applied Biosystems 7700) using specific primer pairs designed for osteoprotegerin using Primer Express software (PE Applied Biosystems) based on the database accession number given by the gene filter manufacturer: osteoprotegerin-112F 5' CTG CGC GCT CGT GTT TCT (SEQ ID NO: 5) and osteoprotegerin-185R 5' AAT GAA GGT ACT TTG GAG GAA ACG (SEQ ID NO: 6). Results were normalized to the expression of the housekeeping gene glyceraldehyde 3-phosphate dehydrogenase (GAPDH) in each sample and are expressed as fold changes, determined by dividing the expression value of the abnormal patient sample by the corresponding normal patient sample.

Cloning of the Full cDNA Coding Sequence of Human Osteoprotegerin.

The full length cDNA coding sequence of OPG was then cloned by reverse transcriptase PCR using the following primers based on the cDNA sequence available in the EMBL database (accession number U94332): OPG F 5' CGG GAT CCGCCA CCA TGA ACA AGT TGC TGT GCT (SEQ ID NO: 7) and OPG R 5' AAG CTC GAG TTA TAA GCA GCT TAT TTT (SEQ ID NO: 8) at 50 pmole each in a 50 .mu.l reaction mixture containing 0.3 mM dNTPs, 1 mM MgSO-.sub.4, 5 .mu.l of normal human dermal (foreskin) fibroblast cDNA template (prepared as described above) 5 .mu.l of 10.times.Pfx amplification buffer (Life Technologies) and 1 .mu.l of Platinum Pfx DNA polymerase (Life Technologies). The reaction mixture was heated at 94 C for 2 min then subjected to 35 cycles of PCR as follows: 94.degree. C. 15 s, 55 C for 30 s and 68 C for 1 min. The amplification products were analyzed on 1% agarose gels in 1 .times.TAE buffer (Life Technologies) and PCR products migrating at the predicted molecular mass (1205 bp) were purified from the gel using the Wizard PCR purification kit (Promega).

One hundred ng of gel-purified DNA was digested with restriction enzymes BamHI and XhoI (Pharmacia), according to the manufacturer's conditions, re-purified as described above and ligated to BamHI/XhoI digested plasmid pcDNA3.1(+) (Invitrogen) using T4 DNA ligase (New England Biolabs) according to standard molecular biology techniques. Ligation products were transformed into E. coli strain TOP 10 F' (Invitrogen) by electroporation using a Biorad Gene Pulser. Plasmid DNA was isolated from 5 ml cultures grown up from the resultant colonies and subjected to automated sequence analysis on an Applied Biosystems 3700 sequencer using T7 and pcDNA3.1AS primers (Invitrogen) to confirm the sequence of OPG.

Detection of Osteoprotegerin in Protein Extracts Isolated from Lesional and Normal Dermal Fibroblasts.

Low passage lesional and normal fibroblasts from scleroderma patients and control subjects, cultured as described above were harvested by treatment of the cell monolayers with PBS containing 1 mM EDTA for 5 min at 37 C. The detached cells were recovered by centrifugation, resuspended in 50 µl of PBS and treated with 50 µl of sample buffer (20% SDS, 0.2% bromophenol blue, 50% glycerol, 1M Tris pH 6.8), frozen at −80° C. and then thawed. Protein content was determined using a BCA kit (Pierce) according to the manufacturer's protocol. Approximately 10 µg protein was treated with 0.1 volume of DTT (0.1M) and run on 4-12% SDS polyacrylamide gels (Novex) according to the manufacturer's instructions. Protein bands were then transferred to nitrocellulose membranes using a Novex wetblot apparatus at 30 V for 1 h. Membranes were then blocked overnight at 4 C in PBS containing 5% defatted milk powder then washed in PBST. Membranes were incubated with primary antibody (R&D systems, anti OPG monoclonal antibody, cat no. MAB8051) at 0.5 µg/ml in PBST/1% BSA for 1 h at room temperature with shaking. After this time membranes were washed extensively with PBST prior to incubation with secondary antibody (anti-mouse horseradish peroxidase, Sigma) at a 1/3000 dilution, in PBST/1% BSA. Membranes were finally washed extensively prior to development and visualization, using ECL reagents and Hyperfilm™ from Amersham.

ELISA to Measure Type I Collagen in Cell Culture Supernatatants of Fibroblasts Treated with Recombinant OPG or Following Transfection of OPG/pcDNA3.1 Vector Collagen synthesis was measured in vitro in cultured human fibroblasts using a capture ELISA system as described by Shi-wen et al., (Shi-Wen et al., 1997). Briefly, AG1518 human dermal fibroblasts (purchased from ATCC) were maintained in DMEM medium containing 5% FCS and 2 mM glutamine (Life Technologies). Cells were harvested by trypsinization and seeded at 70% confluence in 48 well cell culture plates (Falcon) in medium containing 5% serum, then transferred to serum free medium 8 h later. After 24 h, medium was removed and replaced with fresh serum free medium containing 50 µM L-ascorbate (Wako Pure Chemical Industries) and increasing concentrations of human recombinant osteoprotegerin (OPG-Fc, purchased from R&D systems). Sixteen hours later, TGFβ1 (PeproTech) was added to the medium to a final concentration of 2 ng/ml, and after a further 24 h, the medium was recovered, centrifuged to remove cell debris, diluted, and subjected to ELISA for type I collagen as described below.

Collagen synthesis was also measured in primary human fibroblasts (OBHC cells) following transfection with OPG cDNA (pcDNA3.1-OPG) or after mock transfection (pcDNA3.1 vector alone) as follows: OBHC cells were harvested by trypsinization and plated at 50% confluence in 48 well plates in complete medium. Plasmids were transfected into OBHC cells using the Fugene V transfection reagent (Roche) according to the manufacturer's instructions. Five hours after transfection, medium was replaced with fresh serum free medium containing L-ascorbate overnight, then treated with TGFβ1 (10 ng/ml) for 24 h as described above.

MaxiSorp plates (Nunc) were coated overnight, at 4° C. with 5 µg/ml goat anti-human type-I collagen (Southern Biotechnology Associates. Inc.) in PBS (pH 7.4). The antibody solution was then removed and plates were blocked with PBS-1% BSA for 1 h at room temperature. Plates were then washed 4 times PBS/0.05% Tween 20 (PBST). Triplicate samples of 100 µl conditioned media were tested. Samples were incubated for 2 h at room temperature (RT) then washed 4× with PBST. Samples were then incubated with a 1:2000 dilution of biotinylated goat anti-human type-I collagen antibody (Southern Biotechnology Associates. Inc.) for 1 h at RT then washed 4× with PBST. Samples were then incubated with a 1/4000 dilution of HRP-streptavidin conjugated antibody (Zymed) for 1 h at RT with shaking. Finally, samples were washed 4× with PBST. OPD substrate (Sigma cat. no. P9187) was added and left for 10 minutes for colour development. The reaction was stopped with 20% $H_2SO_4$ mix and plates read at 496 nm on a Victor$^2$ multilabel counter (Wallac). Results were normalized for cell numbers using CyQuant cell proliferation assay kit (C-7026) from Molecular Probes.

CTGF-SEAP Promoter Assay

A CTGF-SEAP promoter-reporter plasmid was constructed by PCR performed with oligonucleotides 5'-ATCTCGAGGGCCACTCGTCCCTTGTCC (SEQ ID NO: 9) and 5'-ATAAGCTTGGAGTCGCACTGGCTGTCTCC (SEQ ID NO: 10) to amplify the human CTGF (connective tissue growth factor) gene promoter region (788 bp). The gel-purified amplification product was sub-cloned into the pSEAP2-basic (Clontech).

NIH 3T3 fibroblasts (ATCC) were seeded into T-75 flasks and co-transfected with 5 µg of CTGF-SEAP and 1 µg of pcDNA3.1 (Invitrogen) plasmids. The cells were selected on 800 µg/ml of G 418 (Sigma).

Clones with stably integrated CTGF-SEAP promoter-reporter were established, analyzed clones and the most sensitive one was chosen for cell-based assay development.

Cells from this clone (CTGF-SEAP) were plated at 10,000 cells per well in 96-well plates in DMEM containing 0.5% FCS. The next day fresh medium was added with or without different concentrations of TGFβ and OPG (osteoprotegerin) and the cells were incubated for additional 72 hours prior collections of supernatants for the SEAP assay.

SEAP expression was measured according to the manufacturer's protocol (Clontech kit).

In Vivo Studies

Lung fibrosis was induced in male mice (20-25 g) by intratracheal administration of bleomycin (0.075 IU) in saline on day 1. Mice were divided into 3 separate groups of 10 animals. One group received sub cutaneous (s.c) injections of OPG at 5 mg/kg (in saline) daily. A second group received OPG (0.5 mg/kg) s.c. daily. The third group received saline (s.c.) daily. A fourth group comprised age and sex matched untreated naïve mice. Body mass was measured daily and all mice were sacrificed on day 12. Individual lung lobes were isolated for hydroxyproline determination (Smith et al., 1994), or were formalin fixed and paraffin embedded for histology. Lung sections were stained with tri-chrome or picro sirius red for collagen (Bancroft and Stevens) and the extent of fibrosis/lung was scored.

Semi-Quantitative Reverse Transcriptase PCR Analysis of OPG mRNA in Scleroderma Patient Fibroblasts Treated in Vitro with Halofuqinone.

Lesional and non-lesional fibroblasts were maintained in culture as described above. Cell monolayers (70% confluent) were treated with halofuginone ($10^{-8}$ M) (Collgard Pharmaceuticals) for 12 h. After the treatment period, cells were harvested and total RNA was isolated using the Trizol method. One µg of total RNA was then subjected to reverse transcriptase PCR as described above using PCR primers specific for osteoprotegerin (OPG 740 F 5' ACG CCT AAC TGG CTT AGT GT (SEQ ID NO: 11) and OPG 1280R 5' CTG ATT GGA CCT GGT TAC CT SEQ ID NO: 12). After 30 cycles of PCR, reaction products were run on 1% agarose gels stained with ethidium bromide and photographed and analysed using Kodak 1D Digital Science software. PCR products migrating at the predicted molecular weight were then verified to be osteoprotegerin by direct sequencing of the gel extracted DNA. As a control for genomic DNA contamination, PCR reactions were performed on reverse transcriptase reaction mixes which contained the appropriate RNA but no reverse transcriptase. Reverse transcriptase reactions were also amplified with GAPDH specific PCR primers as a positive control for the integrity and quantity of input RNA in the initial reaction.

Type I Collagen α 2 Promoter Activity.

Mouse embryo fibroblasts (πS3 cells) were maintained in DMEM-F12 medium containing 2% FCS and 2 mM glutamine. Cells were harvested by trypsinization and plated at 50% confluence in 48 well cell culture plates. The next day cells were transfected in serum free medium with pGL3 vector (Promega) containing 3.5 kb of collagen 1α2 promoter linked to luciferase cDNA (kindly provided by Dr. David Abraham from the Royal Free Hospital, London, England) using the Fugene V reagent (Roche) according to the manufacturer's instruction. After 5 h transfection, cells were transferred to fresh medium containing 2% FCS and treated with halofuginone alone ($10^{-10}$ M), TGFβ1 (5 ng/ml) alone or HF ($10^{-8}$ M)+TGFβ1 (5 ng/ml) for 12 h in the presence of 0, 1, 10 or 100 ng/ml of recombinant human osteoprotegerin. After the treatment period, cells were transferred to complete medium containing 2% FCS and 2 mM glutamine and luciferase activity was measured 48 h later in each well, using the Bright-Glo assay system purchased from Promega. Results are expressed as relative luminescence units and were normalized to the number of cells/well determined in a parallel experiment using the Cyquant kit (Molecular Probes).

Example 1

Osteoprotegerin mRNA is Significantly Down Regulated in Lesional Versus Non-Lesional Fibroblasts Gene filter microarray analysis was performed on normal and abnormal fibroblast samples from 6 scleroderma patients. The mean expression level of osteoprotegerin (OPG) is shown in FIG. 1a and for each patient in FIG. 1b.

Figure 2:
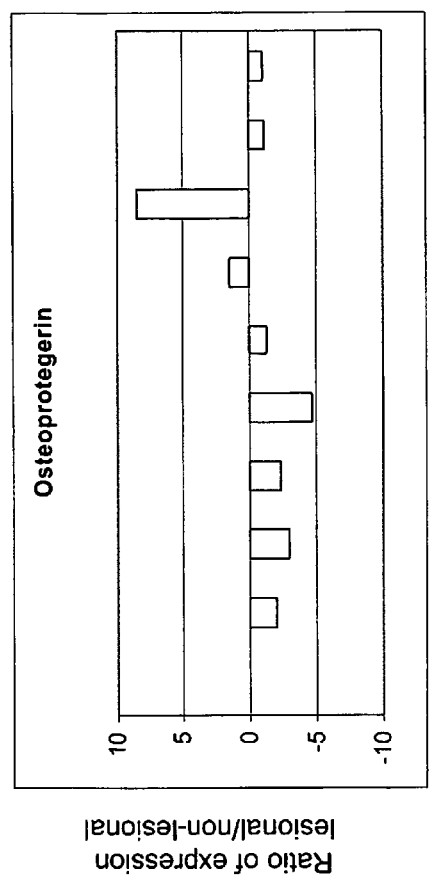
FIG. 2 Real time PCR analysis of OPG mRNA in 9 scleroderma patients. For each patient, results are expressed as the ratio of expression of OPG mRNA in lesional/non-lesional fibroblasts.

The results obtained on the microarrays were further corroborated by real time PCR analysis of RNA samples isolated from 9 patients using OPG specific PCR primers. Results are shown in FIG. 2 and are expressed as the fold change in expression level (lesional divided by non-lesional). In 7 out of the 9 patients tested, OPG was downregulated at least 2 fold in lesional fibroblasts compared to non-lesional fibroblasts isolated from the same patient.

Figure 3:
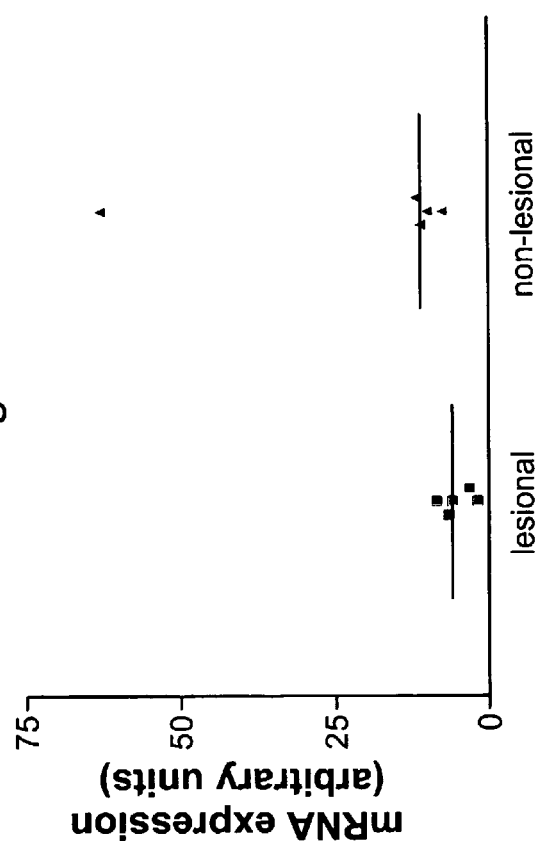
FIG. 3 OPG mRNA expression in biopsies taken from lesional and non-lesional skin in 5 scleroderma patients determined by real time PCR. Bars denote the median expression value for each group.

The differences in expression observed between non-lesional and lesional fibroblasts from the same patient are unlikely to be due differences in the culture conditions between the two populations since OPG mRNA expression in primary cultures of normal human dermal fibroblasts does not change significantly on passaging the cells (data not shown). In addition real time RT-PCR analysis of total RNA isolated from whole biopsy specimens of abnormal skin from scleroderma patients indicated lower levels of osteoprotegerin mRNA compared to clinically normal looking anatomical site matched skin, from the same patients (FIG. 3).

Example 2

Figure 4:
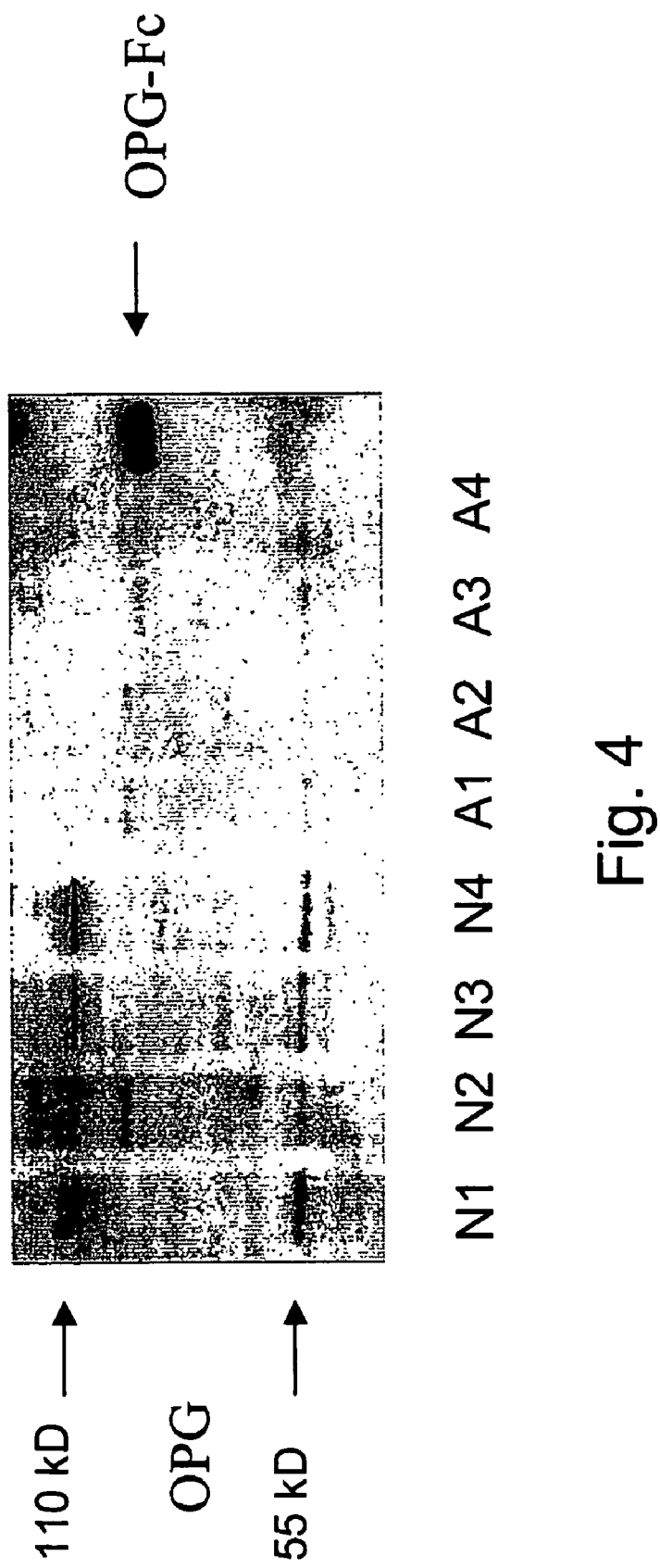
FIG. 4 Western blot analysis of OPG expression in lesional and normal skin fibroblasts. Lesional fibroblasts (A1-A4) and normal fibroblasts (N1-N4). Arrows on the left hand side of the gel indicate the position of native OPG (a 55 kDa monomer) and its dimeric form (110 kDa). OPG Fc fusion protein (purchased from R&D systems) was used as a positive control for the antibody.

OPG is Downregulated at the Protein Level in Lesional vs. Non Lesional Fibroblasts from Scleroderma Patients In order to determine if the downregulation of osteoprotegerin mRNA reflected a change in osteoprotegerin protein, the OPG content of anatomical site matched normal and lesional skin fibroblasts from age and sex matched subjects was determined by Western Blot analysis using anti-human osteoprotegerin monoclonal antibodies. Results are shown in FIG. 4. Osteoprotegrin monomer and dimer were clearly detectable in ¾ normal fibroblasts and weakly expressed in 1 normal sample. In the abnormal fibroblasts a monomeric band was weakly visible in all four samples tested. Recombinantly expressed OPG-Fc fusion protein served as positive control for the staining.

Example 3

Cloning of Human OPG

In order to characterise OPG activity in vitro and in vivo the full cDNA coding sequence was cloned by reverse transcriptase PCR using primers based on the published sequence of OPG, which flanked the predicted start and stop codons. Sequence analysis of the resultant OPG cDNA clones (in pcDNA3.1) revealed 100% identity at the nucleotide level to sequence of OPG published by Morinaga et al., (Morianga et al., 1998) but differed by 1 amino acid to the sequence published by Simonet et al. (1997) (see SEQ ID NO: 2 and 4).

Example 4

Effect on OPG Type I Collagen Synthesis in a Human Dermal Fibroblast Cell Line

Figure 5:
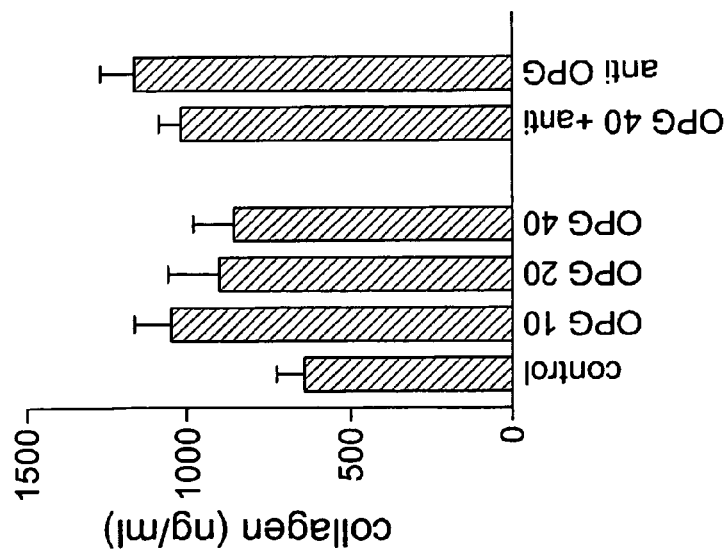
FIG. 5 Effect of OPG on collagen synthesis in AG1518 human fibroblasts. AG1518 cells were either completely untreated or pretreated with 10, 20 or 40 ng/ml OPG for 24 h, or with 40 ng OPG+anti OPG neutralising monoclonal antibody (1 µg/ml), or with anti OPG neutralising monoclonal antibody alone followed by 2 ng/ml TGFβ1 for 24 h. Collagen synthesis was determined by ELISA. Results are the mean of triplicate determinations+S.E.M.

Fibroblasts cultured in the presence of L-ascorbate secrete collagen into the culture medium allowing collagen detection by ELISA. Human fibroblasts upregulate collagen synthesis in response to stimulation with the profibrotic cytokine TGFβ1. We therefore tested the effect of recombinant osteoprotegerin (osteoprotegerin-Fc fusion protein) on TGFβ1 induced collagen synthesis in AG1518C fibroblasts. osteoprotegerin added to fibroblast cultures prior to TGFβ1 treatment was able to inhibit the TGFβ1 mediated increase in collagen synthesis in a dose dependent manner (FIG. 5). When the experiment was performed in the presence of neutralizing anti OPG monoclonal antibodies there was no effect on collagen synthesis. Similarly, administration of anti OPG alone in the absence of recombinant OPG had no effect on collagen synthesis suggesting that the decrease in collagen synthesis observed was a specific effect of OPG.

Figure 6:
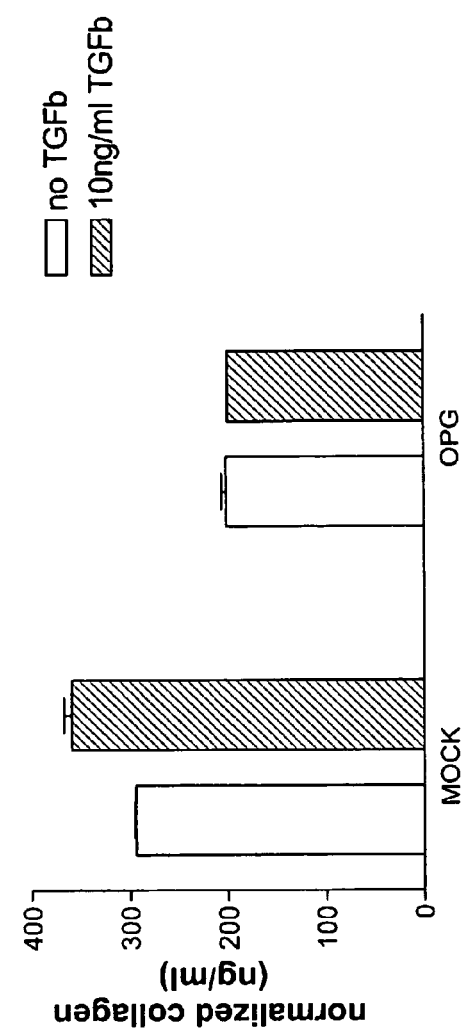
FIG. 6 Effect of OPG transfection on type I collagen α2 synthesis in human primary fibroblasts (OBHC cells). OBHC cells were transfected with pcDNA3.1/OPG (OPG) or pcDNA3.1 alone (mock) as described in methods. Collagen in conditioned medium was measured 24 h after TGFβ1 treatment by ELISA. Results are the mean of triplicate determinations±S.E.M.

A similar effect was observed on collagen synthesis upon transfection of primary human fibroblasts (OBHC) with a plasmid containing the full coding sequence of OPG (pcDNA3.1/OPG). In OBHC transfected with OPG plasmid, no increase in collagen synthesis was observed in response to TGFβ1 stimulation, in contrast to mock (pcDNA3.1 empty vector) transfected OBHC (FIG. 6).

Example 5

OPG Treatment Significantly Decreases Both Basal and TGFβ1 Induced Type 1 Collagen Alpha 2 Promoter Activity in Mouse Embryo Fibroblasts In order to evaluate if the decrease in collagen synthesis by OPG was due to an effect on collagen promoter activity we examined the effect of OPG treatment on mouse embryo fibroblasts which had been transfected with a plasmid which contained a reporter gene cDNA, luciferase, under the control of a 3.5 kb region of the type I collagen α2 promoter. Stimulation of the collagen promoter in this construct leads to transcriptional activation of the luciferase gene whose activity can be measured in the presence of its substrate firefly luciferin by luminescence assay.

Figure 7A:
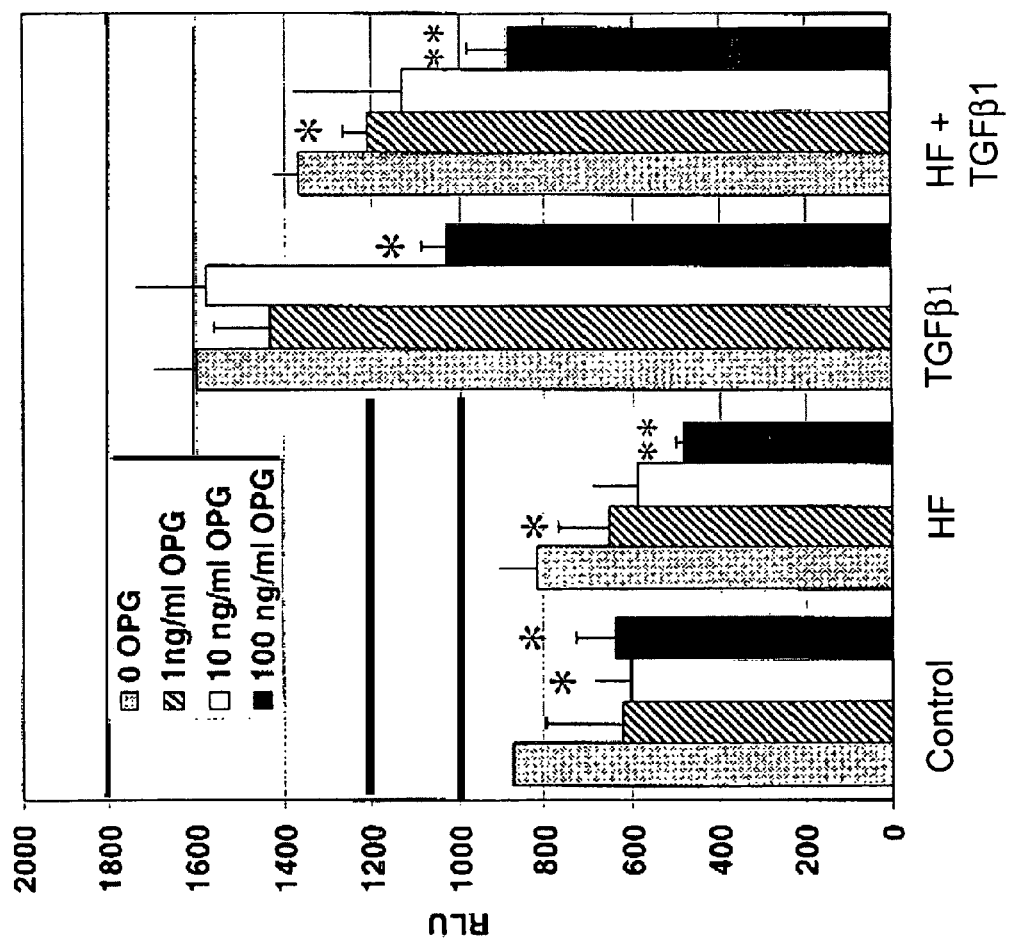
FIG. 7A: Effect of OPG on type 1 collagen α2 promoter activity in mouse embryo fibroblasts. Mouse embryo fibroblasts (πS3 cells) were transfected with pGL3 vector containing 3.5 kb of collagen 1α2 promoter linked to luciferase cDNA. After transfection, cells were transferred to fresh medium and were either untreated (control) or treated with of halofuginone ($10^{-10}$ M) alone (HF); TGFβ1 (5 ng/ml) (TGFβ1); or TGFβ1 (5 ng/ml)+HF ($10^{-8}$ M) (HF+TGFβ1) for 12 h with increasing concentrations of osteoprotegerin. Results are the mean of triplicate determinations. * denotes P<0.05 and ** denotes P<0.01.

Treatment with OPG from 1 ng/ml to 100 ng/ml was able to significantly decrease the basal level of collagen promoter activity (FIG. 7A, control). Following TGFβ1 stimulation there was at least a 2 fold increase in collagen promoter activity (FIG. 7A, TGFβ1). This could be significantly decreased when the cells were concurrently treated with OPG at 100 ng/ml ($P \leq 0.05$).

The plant alkaloid halofuginone has been reported to be a specific inhibitor of type I collagen synthesis (Granot et al., 1993). When fibroblasts were treated with low concentrations of halofuginone ($10^{-10}$ M) we observed a dose dependent decrease in collagen promoter activity with increasing concentrations of osteoprotegerin (from 1 ng/ml to 100 ng/ml) which was highly significant at the highest dose of OPG tested (100 ng/ml, $P \leq 0.01$) (FIG. 7A, HF). Halofuginone can inhibit TGFβ1 induced collagen promoter activity (McGaha et al 2002). OPG was also able to potentiate the effects of halofuginone by inhibiting the TGFβ1 induced increase in collagen promoter activity in a dose dependent manner. This effect was highly significant at 100 ng/ml OPG ($P \leq 0.01$) at which concentration the collagen promoter activity was almost returned to basal levels (FIG. 7, HF+TGFβ1).

Example 6

TGFβ Mediated Transactivation of Connective Tissue Growth Factor is Counteracted by OPG Connective tissue growth factor (CTGF) a 38-kD cysteine-rich protein, stimulates the production of extracellular matrix elements by fibroblasts. CTGF overexpression has been reportedly found in many fibrotic human tissues, including lung, skin, liver, kidney and blood vessels. In vitro, TGFβ activates CTGF gene transcription in human lung fibroblasts. A CTGF promoter-reporter was constructed with secreted alkaline phosphotase (SEAP) as a reporter, expression of which can be measured in the conditioned medium instead of a cell extract.

Figure 7B:
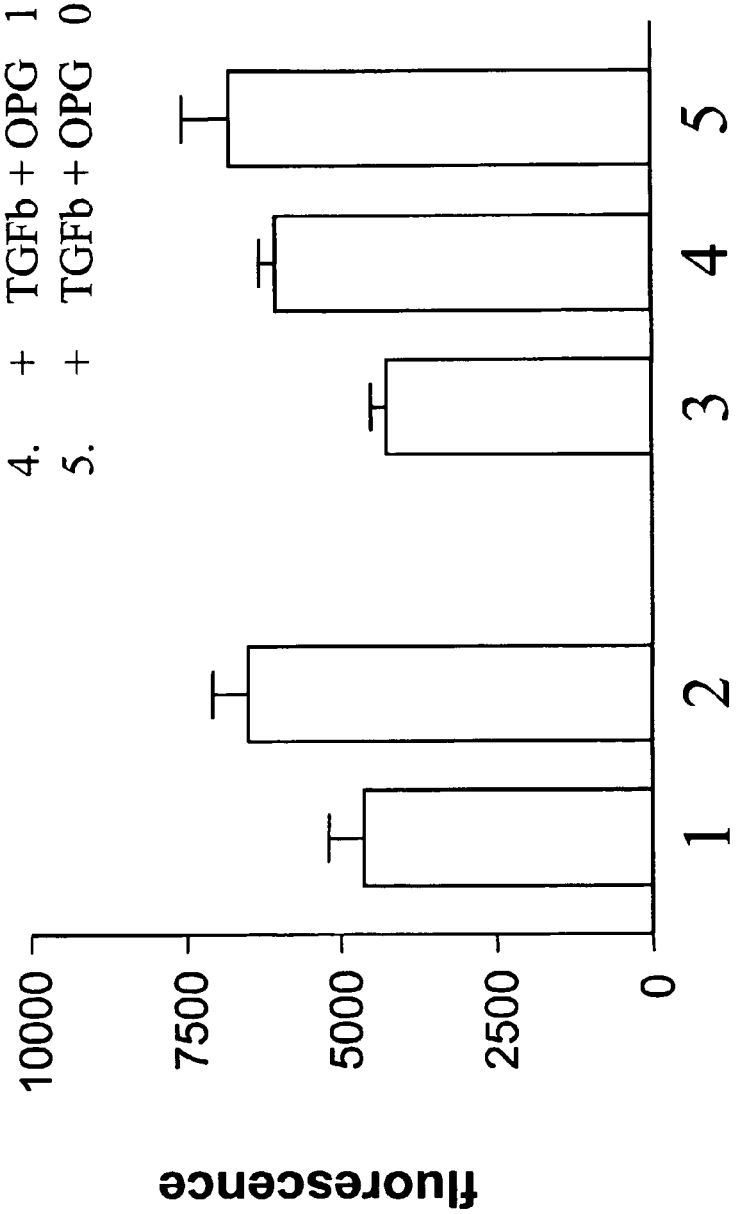
FIG. 7B shows the extent of reporter gene expression under the CTGF promoter after incubation with either TGFβ alone or in combination with different amounts of OPG.

Cells expression the CTGF-SEAP reporter gene were incubated with TGFβ and 0.46, 1.4 or 4.6 μg/ml of OPG. The results of this experiment are depicted in FIG. 7B. Incubation with OPG repressed TGFβ induced CTGF expression, thus further indicating an anti-fibrotic activity of OPG.

Example 7

Expression of OPG mRNA in Halofuginone Treated Scleroderma Patient Fibroblasts

The mechanism by which halofuginone is able to down regulate collagen synthesis in fibroblasts has not been fully elucidated. We therefore examined the effect of halofuginone on the expression of OPG mRNA in paired lesional and non-lesional fibroblasts from scleroderma patients by reverse transcriptase PCR.

Figure 8:
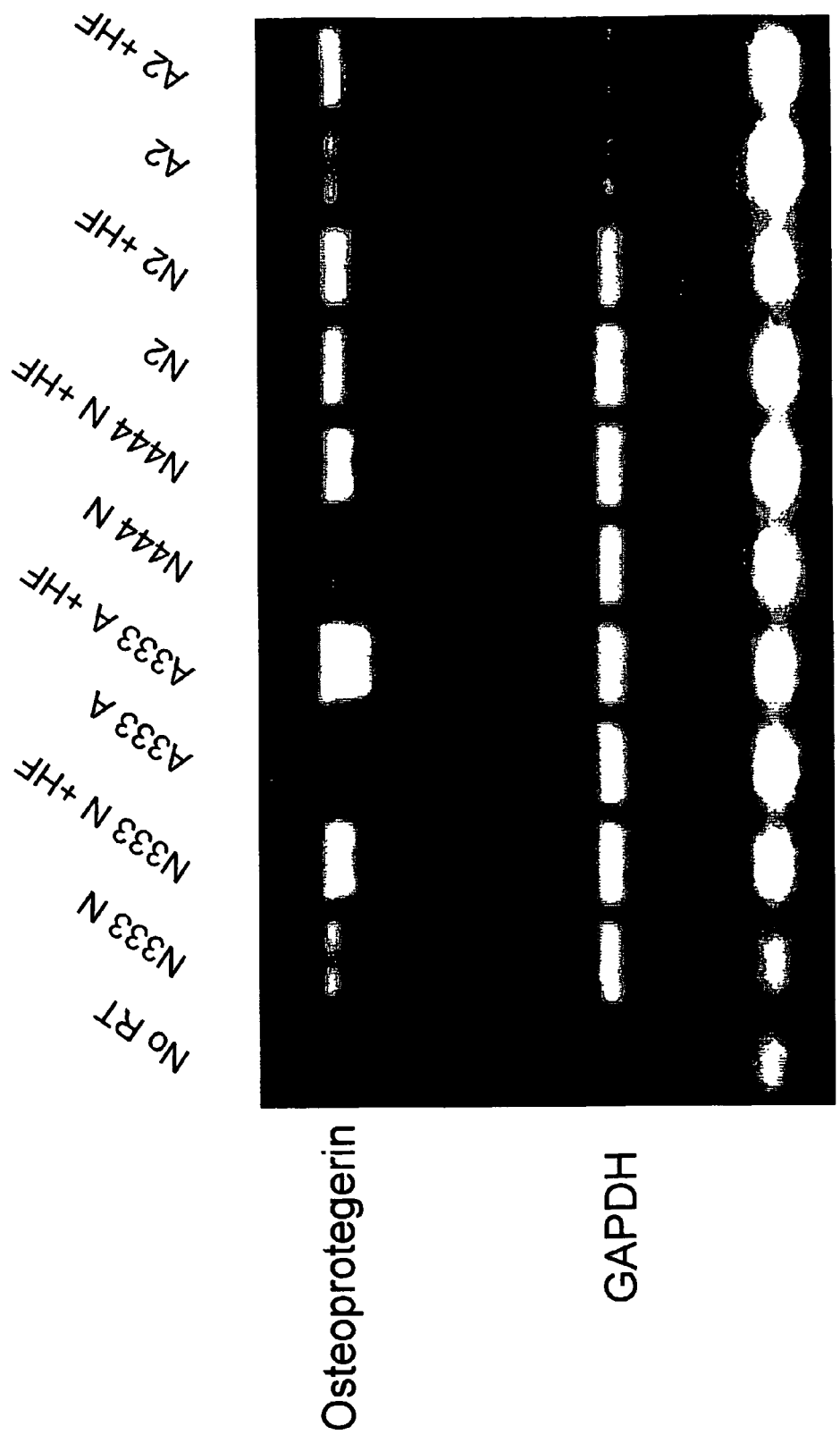
FIG. 8 Reverse transcriptase PCR analysis of osteoprotegerin mRNA after in vitro treatment of lesional and non-lesional fibroblasts from scleroderma patients with halofuginone. One % agarose—ethidium bromide stained gel showing RT PCR reaction products for osteoprotegrin (top) and GAPDH (bottom) in lesional (suffix A), or non-lesional (suffix N), fibroblasts.

OPG mRNA expression is highly upregulated (at least 3 fold) in both lesional and non lesional fibroblasts in all samples tested (3 normals and 2 abnormals) when measured 12 h after treatment with $10^{-8}$ M halofuginone (FIG. 8). Interestingly, in gene filter microarray analysis experiments OPG was one of the most upregulated genes on treatment of fibroblasts with halofuginone (data not shown).

Example 8

OPG Administration in Vivo Protects Against Bleomycin Induced Lung Fibrosis in Mice Administration of a single intra-tracheal injection bleomycin to C57BL/6 mice results in the rapid induction of pulmonary fibrosis within 14 days, which is characterized by increased collagen deposition within the lung interstitium (Hattori et al., 2000). In order to determine if OPG administration could have any protective effect against the development of fibrosis or indeed reduce the severity of the disease, we tested the effect of daily injection of OPG in bleomycin treated mice.

Bleomycin was administered by a single intra-tracheal instillation to 3 groups of 10 mice. OPG was administered by subcutaneous injection starting the day after bleomycin treatment. One group received a high dose (5 mg/kg) and the second group received a lower dose (0.5 mg/kg). Control mice received saline s.c. daily. For comparison a $4^{th}$ group of mice was included in the study which comprised completely untreated, age and sex matched individuals (naïve mice).

Figure 9:
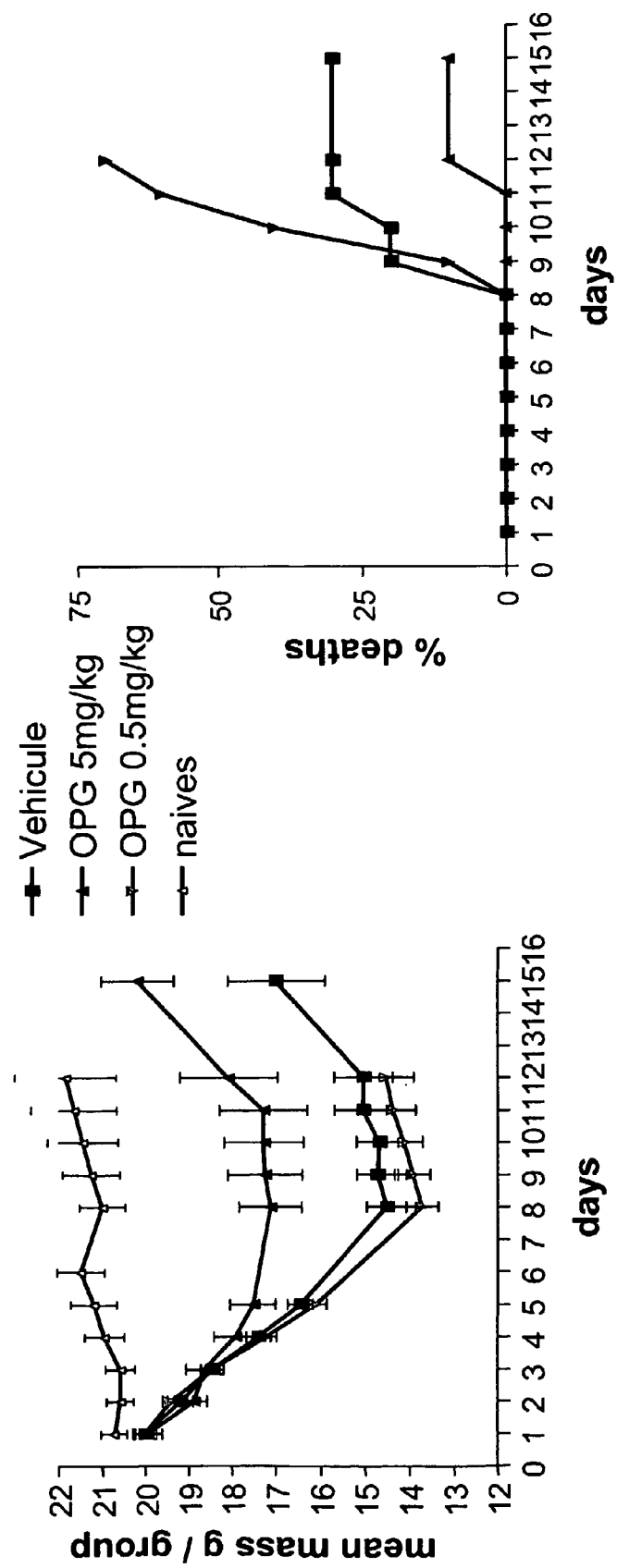
FIG. 9 Effect of in vivo administration of osteoprotegerin on the development of lung fibrosis in bleomycin treated mice. A: Change in mouse body mass following treatment with osteoprotegerin. Results are expressed as the mean mass in g/group measured each day after intra-tracheal instillation of bleomycin. B: Mortality resulting from bleomycin administration. Results are expressed as a percentage of the number of deaths per group of 10 animals.

Animals treated with bleomycin fall sick immediately. This results in a rapid loss of body mass and can lead to death, in contrast to untreated animals which remain happy and healthy and show normal weight gain (FIG. 9A). Mice treated with the low dose of OPG showed a comparable weight loss to the control animals. There also appeared to be increased mortality in this group (FIG. 9B). Mice receiving the high dose of OPG fared much better, with a decline in body mass only for the first 5 days of treatment. This also reflected the low mortality (<10%) in this group.

Figure 10:
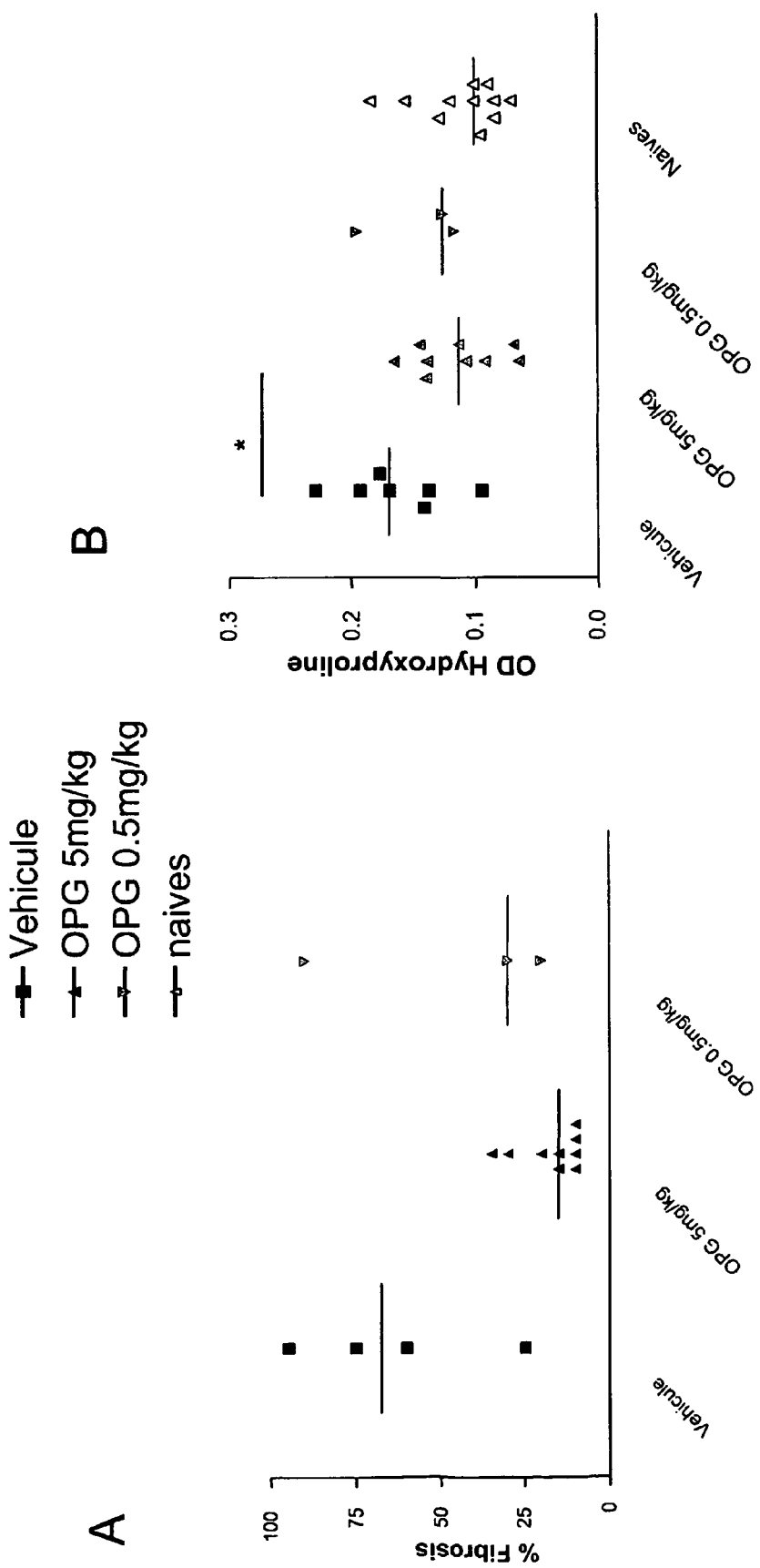
FIG. 10 Effect of in vivo administration of osteoprotegerin on the development of lung fibrosis in bleomycin treated mice. A: Extent of fibrosis in the lungs measured 12 days after bleomycin administration. Lungs were stained with trichrome. Results are expressed as the % of a representative lung lobe affected by fibrosis for each surviving animal. B: Extent of collagen deposition in the lungs measured 12 days after bleomycin administration. Hydroxyproline content was measured in a representative lung lobe taken from each surviving animal.

All surviving mice were sacrificed 12 days after the bleomycin treatment. Histological analysis of lungs revealed that in the high dose OPG treated animals there was significantly less lung surface area affected by fibrosis compared to control animals which had fibrotic lesions covering approx. 70% of the lung surface (FIG. 10A). High dose OPG treated mice also showed significantly less hydroxyproline content in the lungs ($P \leq 0.05$) compared to control mice and was comparable to that seen in the untreated mice (naïve group, FIG. 10B)). Reduced hydroxyproline content was also observed in the low dose OPG treated mice, although this did not reach statistical significance due to the small number of survivors left in this group. Hydroxyproline content is a measure of collagen deposition. The results here indicate that OPG treatment effectively leads to reduced collagen deposition in the lungs.

REFERENCES

1. Abraham D., Lupoli S., McWhirter A., Plater-Zyberk C., Piela T. H., Korn J. H., Olsen I. and Black C. (1991) Expression and function of surface antigens on scleroderma fibroblasts. Arthritis Rheum. 34, 1164-1172.
2. Abraham D J, Shiwen X, Black C M, Sa S, Xu Y, Leask A. J Biol Chem. 2000 May 19; 275(20): 15220-5.
3. Altschul S F et al, J Mol Biol, 215, 403-410, 1990
4. Altschul S F et al, Nucleic Acids Res., 25:389-3402, 1997
5. Bancroft J. D. and Stevens A. Theory and Practice of Histological Techniques. Churchill Livingstone, England.
6. Black C. M and Denton C. P. (1998) Systemic sclerosis and related disorders. In "Oxford textbook of Rheumatology"

(P. G. Maddison, D. A. Isenberg, P. Woo and D. N. Glass, Eds.) pp 771-789, Oxford Univ. Press, New York.
7. Clements P. J. and Furst D. E. (1996) "Systemic Sclerosis" Williama and Williams, Baltimore.
8. Devereux J et al, Nucleic Acids Res, 12, 387-395, 1984.
9. Engelmann, H., Novick, D., and Wallach, D., 1990, J. Biol. Chem. 265, 1531-1536.
10. Granot I, Halevy O, Hurwitz S, Pines M. (1993) Halofuginone: an inhibitor of collagen type I synthesis. Biochim Biophys Acta 1156, 107-112
11. Grantham (1974), Science, 185. 862-864.
12. Hattori N., Degen J. L., Sisson T. H., Liu H., Moore B. B., Pandrangi R. G., Simon R. H. and Drew A. F. (2000) Bleomycin induced pulmonary fibrosis in fibrinogen null mice. J. Clin. Invest. 106, 1341-135
13. Kostenuik P J, Shalhoub V. Curr Pharm Des May 2001; 7(8):613-35
14. Krein, P M, Huang Y amd Winston B W (2001). Expert Opin. Ther. Patents 11(7): 1065-1079.
15. Leighton, C. Drugs 2001 61(3), 419-427.
16. LeRoy E. C. (1974) Increased collagen synthesis by scleroderma skin fibroblasts in vitro. J. Clin. Invest. 54, 880-889.
17. Martini, Maccario, Ravelli et al., Arthritis Rheum. 1999, 42, 807-811.
18. McGaha T L, Phelps R G, Spiera H, Bona C. (2002) Halofuginone, an Inhibitor of Type-I Collagen Synthesis and Skin Sclerosis, Blocks Transforming-Growth-Factor-beta-Metiated Smad3 Activation in Fibroblasts. J Invest Dermatol. 118,461-70.
19. Min H., Morony S., Sarosi I., Dunstan C. R., Capparelli C. et al (2000) Osteoprotegerin reverses osteoporosis by inhibiting endosteal osteoclasts and prevents vascular calcification by blocking a process resembling osteoclastogenesis. J. Exp. Med. 192, 463-474.
20. Morinaga T., Nagakawa N., Yasuda H., Tsuda E. and Higashi K. (1998) Cloning and characterization of the gene encoding human osteoprotegerin/osteoclastogenesis inhibitory factor. Eur. J. Biochem. 254, 685-691.
21. Pearson W R, Methods in Enzymology, 183, 63-99,1990
22. Pearson W R and Lipman D J, Proc Nat Acad Sci USA, 85, 2444-2448, 1988
23. Silman A. J. (1991) Moratlity from scleroderma in England and Wales 1968-1975. Ann. Rheu. Dis. 50, 95-96.
24. Simonet W. S., Lacey D., Dunstan C. R., Kelley M., et al. (1997) Osteoprotegerin: a novel secreted protein involved in the regulation of bone densit y. Cell 89, 309-319.
25. Shi-wen X., Denton C. P., McWhirter A., Bou-Gharios G., Abraham D. J., du Bois R. M. and Black C. M. (1997) Scleroderma lung fibroblasts exhibit elevated and dysregulated collagen type I biosynthesis. Arthritis Rheum. 40, 1237-1244.
26. Shi-Wen X, Denton C P, McWhirter A, Bou-Gharios G, Abraham D J, du Bois R M, Black C M. (1997) Scleroderma lung fibroblasts exhibit elevated and dysregulated type I collagen biosynthesis. Arthritis Rheum. 40, 1237-1244
27. Smith and Waterman J Mol Biol, 147, 195-197, 1981, Advances in Applied Mathematics, 2, 482-489, 1981.
28. Smith R. E., Strieter R. M., Phan S. H., Lukacs N. W., Huffnagle G. B., Wilke C. A., Burdick M. D., Lincoln P., Evanoff H. and Kunkel S. L. (1994) Production and function of murine macrophage inflammatory protein-1α in bleomycin induced lung injury. J. Immunol. 153, 4704.
29. Smith, Textbook of the Autoimmune Diseases, Edited by Lahita, Chiorazzi and Reeves, Lippincott Williams & Wilkins, Philadelphia 2000.
30. Strehlow D. and Korn J (1998) Biology of the scleroderma fibroblast. Curr. Opin. Rheumatol. 10, 572-578.
31. Tucci, A., James, H., Chicheportiche, R., Bonnefoy, J. Y., Dayer, J. M., and Zubler, R. H., 1992, J. Immunol. 148, 2778-2784.
32. Von Heijne G. (1986) Nucleic Acids Res. 14, 4683-4690.
33. Wigley F. M. and Sule S. D. (2001) Expert Opinions on Investigational Drugs 10(1) 31-48.
34. Wigley F. M. and Boling C. L. (2000) The treatment of scleroderma. 2, 276-292.
35. Wilm M., Shevchenko A., Houthaeve T., Breit S., Schweigerer L., Fotsis T. and Mann M. (1996) Femtomole sequencing of proteins from polyacrylamide gels by nano-electrospray mass spectrometry. *Nature,* 379:466-469
36. Yasuda H., Shima N., Nagakawa N., Mochizuki S., Yano K. et al (1998) Identity of osteoclastogenesisis inhibitory factor (OCIF) and osteoprotegerin (OPG): a mechanism by which OPG/OCIF inhibits osteoclastogenesis in vitro. Endocrinology 139, 1329-1337.

The invention claimed is:

1. A method for treating or inhibiting progression or treating symptoms of a fibrotic disease selected from a connective tissue disease, scleroderma, fibrosis of the skin, Dupuytren's contracture, keloid, scarring and fibrosis of the pancreas comprising administering to a patient in need of treatment thereof a therapeutically effective amount of a substance selected from the group consisting of:
   a) a polypeptide comprising SEQ ID NO: 2 or SEQ ID NO: 4;
   b) a polypeptide comprising amino acids 22 to 401 of SEQ ID NO: 2 or SEQ ID NO: 4;
   c) a polypeptide comprising amino acids 22 to 194 of SEQ ID NO: 2 or SEQ ID NO: 4;
   d) a mutein of any of (a) to (c), wherein the amino acid sequence has at least 90% identity to at least one of the sequences in (a) to (c);
   e) a mutein of any of (a) to (c) which is encoded by a DNA sequence which hybridizes to the complement of the DNA sequence encoding any of (a) to (c) under washing conditions of 12-20° C. below the calculated Tm of the hybrid of the DNA sequence of the mutein and the complement in 2×SSC and 0.5% SDS for 5 minutes and which reduces collagen synthesis; and
   f) a salt or fused protein of any of (a) to (e).

2. The method of claim 1, wherein the fibrotic disease is a connective tissue disease.

3. The method of claim 1, wherein the fibrotic disease is scleroderma.

4. The method of claim 1, wherein the substance is a monomer or dimer.

5. The method of claim 4, wherein the substance is glycosylated at one or more sites.

6. The method of claim 5, wherein the substance is a fused protein and wherein the fused protein comprises an immunoglobulin (Ig) fusion.

7. The method of claim 6, wherein the Ig fusion is an Fc fusion.

8. The method of claim 1, wherein the substance comprises at least one moiety attached to one or more functional groups, which occur at one or more side chains on the amino acid residues.

9. The method of claim 8, wherein the moiety is a polyethylene glycol moiety.

10. The method of claim 1, wherein the substance is produced by an isolated cell.

11. The method of claim 1, wherein the substance is produced by an isolated cell genetically modified to produce said substance.

12. The method of claim 1, further comprising simultaneously, sequentially, or separately administering an interferon.

13. The method of claim 12, wherein the interferon is interferon-β.

14. The method of claim 1, further comprising simultaneously, sequentially, or separately administering a Tumor Necrosis Factor (TNF) antagonist.

15. The method of claim 14, wherein the TNF antagonist is TBPI, TBPII or both TBPI and TBPII.

16. The method of claim 1, further comprising simultaneously, sequentially, or separately administering an anti-scleroderma agent.

17. The method of claim 16, wherein the anti-scleroderma agent is selected from the group consisting of halofuginone, ACE inhibitors, calcium channel blockers, proton pump inhibitors, non-steroidal anti-inflammatory drugs, COX-inhibitors, corticosteroids, tetracycline, pentoxifylline, bucillamine, geranylgeranyl transferase inhibitors, rotterlin, prolyl-4-hydroxlase inhibitors, c-proteinase inhibitors, lysyl-oxidase inhibitors, relaxin, prostaglandins, prostacyclins, endothelin-1, nitric oxide, angiotensin II inhibitors, anti-oxidants and SARP-1.

18. The method of claim 16, wherein the fibrotic disease is a connective tissue disease.

19. The method of claim 16, wherein the fibrotic disease is scleroderma.

20. The method of claim 1, wherein progression and symptoms are inhibited.

* * * * *

UNITED STATES PATENT AND TRADEMARK OFFICE
CERTIFICATE OF CORRECTION

PATENT NO. : 7,638,480 B2
APPLICATION NO. : 10/510876
DATED : December 29, 2009
INVENTOR(S) : Power et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1062 days.

Signed and Sealed this

Twelfth Day of October, 2010

David J. Kappos
*Director of the United States Patent and Trademark Office*

```
                        SEQUENCE LISTING

<160> NUMBER OF SEQ ID NOS: 12

<210> SEQ ID NO 1
<211> LENGTH: 1681
<212> TYPE: DNA
<213> ORGANISM: Homo sapiens

<400> SEQUENCE: 1
ctggagacat ataacttgaa cacttggccc tgatggggaa gcagctctgc agggactttt      60
tcagccatct gtaaacaatt tcagtggcaa cccgcgaact gtaatccatg aatgggacca     120
cactttacaa gtcatcaagt ctaacttcta gaccaggaa ttaatggggg agacagcgaa     180
ccctagagca aagtgccaaa cttctgtcga tagcttgagg ctagtggaaa gacctcgagg    240
aggctactcc agaagttcag cgcgtaggaa gctccgatac caatagccct ttgatgatgg    300
tggggttggt gaagggaaca gtgctccgca aggttatccc tgcccaggc agtccaattt     360
```

-continued

```
tcactctgca gattctctct ggctctaact accccagata caaggagtg aatgcagaat    420
agcacgggct ttagggccaa tcagacatta gttagaaaaa ttcctactac atggtttatg    480
taaacttgaa gatgaatgat tgcgaactcc ccgaaaaggg ctcagacaat gccatgcata    540
aagagggggcc ctgtaatttg aggtttcaga acccgaagtg aagggggtcag gcagccgggt   600
acggcggaaa ctcacagctt tcgcccagcg agaggacaaa ggtctgggac acactccaac    660
tgcgtccgga tcttggctgg atcggactct cagggtggag gagacacaag cacagcagct    720
gcccagcgtg tgcccagccc tcccaccgct ggtcccggct gccaggaggc tggccgctgg    780
cgggaagggg ccgggaaacc tcagagcccc gcggagacag cagccgcctt gttcctcagc    840
ccggtggctt ttttttcccc tgctctccca ggggacagac accaccgccc cacccctcac    900
gccccacctc cctgggggat cctttccgcc ccagccctga aagcgttaat cctggagctt    960
tctgcacacc ccccgaccgc tcccgcccaa gcttcctaaa aaagaaaggt gcaaagtttg   1020
gtccaggata gaaaaatgac tgatcaaagg caggcgatac ttcctgttgc cgggacgcta   1080
tatataacgt gatgagcgca cgggctgcgg agacgcaccg gagcgctcgc ccagccgccg   1140
cctccaagcc cctgaggttt ccggggacca caatgaacaa gttgctgtgc tgcgcgctcg   1200
tggtaagtcc ctgggccagc cgacgggtgc ccggcgcctg gggaggctgc tgccacctgg   1260
tctcccaacc tccagcgga ccggcgggga gaaggctcca ctcgctccct cccaggagag   1320
gcttggggtt aggctggagc aggaaaccgc tttcaagtta tgccatgctt cccctagggt   1380
gtccttttac gctgcaaagt tcctgctgac tttatggaag acagcaagag agagacagac   1440
agcgagagag agggagagag agagagagag aaacttgttt gaaagtttta gtcattaacc   1500
ttctgtcttc atctcagaat attaacgccc tcatgtagtc catactatct ttgcttaatg   1560
aacttgaact tttattatta gtggcaaaga agtggtccct tagattcaga gtaagttgga   1620
agaagacgtt agtcttctta aaaccattat aattagaata tgacatgata gattttttcta   1680
a                                                                    1681
```

<210> SEQ ID NO 2
<211> LENGTH: 401
<212> TYPE: PRT
<213> ORGANISM: Homo sapiens

<400> SEQUENCE: 2

```
Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125
```

| | | | | | | | | | | | |
|---|---|---|---|---|---|---|---|---|---|---|---|
|Gly|Val|Val|Gln|Ala|Gly|Thr|Pro|Glu|Arg|Asn|Thr|Val|Cys|Lys|Arg|
| |130| | | |135| | | |140| | | | | | |

Gly Val Val Gln Ala Gly Thr Pro Glu Arg Asn Thr Val Cys Lys Arg
        130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Thr Gln Lys
                165                 170                 175

Gly Asn Ala Thr His Asp Asn Ile Cys Ser Gly Asn Ser Glu Ser Thr
                180                 185                 190

Gln Lys Cys Gly Ile Asp Val Thr Leu Cys Glu Glu Ala Phe Phe Arg
            195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Lys His Ser
            340                 345                 350

Lys Thr Tyr His Phe Pro Lys Thr Val Thr Gln Ser Leu Lys Lys Thr
                355                 360                 365

Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Cys
385                 390                 395                 400

Leu

<210> SEQ ID NO 3
<211> LENGTH: 1356
<212> TYPE: DNA
<213> ORGANISM: Homo sapiens

<400> SEQUENCE: 3

```
gtatatataa cgtgatgagc gtacgggtgc ggagacgcac cggagcgctc gcccagccgc      60
cgyctccaag cccctgaggt ttccggggac cacaatgaac aagttgctgt gctgcgcgct     120
cgtgtttctg gacatctcca ttaagtggac cacccaggaa acgtttcctc caaagtacct     180
tcattatgac gaagaaacct ctcatcagct gttgtgtgac aaatgtcctc ctggtaccta     240
cctaaaacaa cactgtacag caaagtggaa gaccgtgtgc gcccctttgcc ctgaccacta     300 ctacacagac agctggcaca ccagtgacga gtgtctatac tgcagccccg tgtgcaagga     360
gctgcagtac gtcaagcagg agtgcaatcg cacccacaac cgcgtgtgcg aatgcaagga     420
agggcgctac cttgagatag agttctgctt gaaacatagg agctgccctc ctggatttgg     480
agtggtgcaa gctggaaccc cagagcgaaa tacagtttgc aaaagatgtc cagatgggtt     540
```

```
cttctcaaat gagacgtcat ctaaagcacc ctgtagaaaa cacacaaatt gcagtgtctt    600
tggtctcctg ctaactcaga aaggaaatgc aacacacgac aacatatgtt ccggaaacag    660
tgaatcaact caaaaatgtg aatagatgt taccctgtgt gaggaggcat tcttcaggtt    720
tgctgttcct acaaagttta cgcctaactg gcttagtgtc ttggtagaca atttgcctgg    780
caccaaagta aacgcagaga gtgtagagag gataaaacgg caacacagct cacaagaaca    840
gactttccag ctgctgaagt tatggaaaca tcaaaacaaa gcccaagata tagtcaagaa    900
gatcatccaa gatattgacc tctgtgaaaa cagcgtgcag cggcacattg acatgctaa    960 cctcaccttc gagcagcttc gtagcttgat ggaaagctta ccgggaaaga agtgggagc   1020 agaagacatt gaaaaaacaa taaaggcatg caaacccagt gaccagatcc tgaagctgct   1080
cagtttgtgg cgaataaaaa atggcgacca agacaccttg aagggcctaa tgcacgcact   1140
aaagcactca aagacgtacc actttcccaa aactgtcact cagagtctaa agaagaccat   1200
caggttcctt cacagcttca caatgtacaa attgtatcag aagttatttt tagaaatgat   1260
aggtaaccag gtccaatcag taaaaataag ctgcttataa ctggaaatgg ccattgagct   1320
gtttcctcac aattggcgag atcccatgga tgataa                             1356
```

<210> SEQ ID NO 4
<211> LENGTH: 401
<212> TYPE: PRT
<213> ORGANISM: Homo sapiens

<400> SEQUENCE: 4

```
Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
                165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
    210                 215                 220
```

```
Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
            245                 250                 255

Trp Lys His Gln Asn Lys Ala Gln Asp Ile Val Lys Lys Ile Ile Gln
            260                 265                 270

Asp Ile Asp Leu Cys Glu Asn Ser Val Gln Arg His Ile Gly His Ala
            275                 280                 285

Asn Leu Thr Phe Glu Gln Leu Arg Ser Leu Met Glu Ser Leu Pro Gly
    290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
            355                 360                 365

Ile Arg Phe Leu His Ser Phe Thr Met Tyr Lys Leu Tyr Gln Lys Leu
            370                 375                 380

Phe Leu Glu Met Ile Gly Asn Gln Val Gln Ser Val Lys Ile Ser Cys
385                 390                 395                 400

Leu

<210> SEQ ID NO 5
<211> LENGTH: 18
<212> TYPE: DNA
<213> ORGANISM: homo sapiens

<400> SEQUENCE: 5
ctgcgcgctc gtgtttct                                                        18

<210> SEQ ID NO 6
<211> LENGTH: 24
<212> TYPE: DNA
<213> ORGANISM: homo sapiens

<400> SEQUENCE: 6
aatgaaggta ctttggagga aacg                                                 24

<210> SEQ ID NO 7
<211> LENGTH: 33
<212> TYPE: DNA
<213> ORGANISM: homo sapiens

<400> SEQUENCE: 7
cgggatccgc caccatgaac aagttgctgt gct                                       33

<210> SEQ ID NO 8
<211> LENGTH: 27
<212> TYPE: DNA
<213> ORGANISM: homo sapiens

<400> SEQUENCE: 8
aagctcgagt tataagcagc ttatttt                                              27
```

```
<210> SEQ ID NO 9
<211> LENGTH: 27
<212> TYPE: DNA
<213> ORGANISM: homo sapiens

<400> SEQUENCE: 9
atctcgaggg ccactcgtcc cttgtcc                                          27

<210> SEQ ID NO 10
<211> LENGTH: 29
<212> TYPE: DNA
<213> ORGANISM: homo sapiens

<400> SEQUENCE: 10
ataagcttgg agtcgcactg gctgtctcc                                        29

<210> SEQ ID NO 11
<211> LENGTH: 20
<212> TYPE: DNA
<213> ORGANISM: homo sapiens

<400> SEQUENCE: 11
acgcctaact ggcttagtgt                                                  20

<210> SEQ ID NO 12
<211> LENGTH: 20
<212> TYPE: DNA
<213> ORGANISM: homo sapiens

<400> SEQUENCE: 12
ctgattggac ctggttacct                                                  20
```